US009718772B2

(12) United States Patent
Chollet

(10) Patent No.: US 9,718,772 B2
(45) Date of Patent: Aug. 1, 2017

(54) CRYSTALLINE (3Z,5S)-5-(HYDROXYMETHYL)-1-[(2'-METHYL-1,1'-BIPHENYL-4-YL)CARBONYL] PYRROLIDIN-3-ONE O-METHYLOXIME, AND METHODS OF USING THE SAME

(71) Applicant: ObsEva SA, Plan-les-Ouates (CH)

(72) Inventor: André Chollet, Plan-les-Ouates (CH)

(73) Assignee: ObsEva S.A., Plan-les-Ouates (CH)

( * ) Notice: Subject to any disclaimer, the term of this patent is extended or adjusted under 35 U.S.C. 154(b) by 0 days.

(21) Appl. No.: 14/735,215

(22) Filed: Jun. 10, 2015

(65) Prior Publication Data

US 2016/0002160 A1 Jan. 7, 2016

Related U.S. Application Data

(60) Provisional application No. 62/020,076, filed on Jul. 2, 2014.

(51) Int. Cl.
C07D 207/22 (2006.01)

(52) U.S. Cl.
CPC ........ *C07D 207/22* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,047,247 A | 9/1991 | Milovac et al. | |
| 5,069,910 A | 12/1991 | Kovacic et al. | |
| 7,115,754 B2 | 10/2006 | Jorand-Lebrun et al. | |
| 7,211,601 B2 | 5/2007 | Halazy et | |
| 2003/0105030 A1 | 6/2003 | Liao et al. | |
| 2003/0180532 A1 | 9/2003 | Patel et al. | |
| 2004/0147511 A1 | 7/2004 | Schwarz et al. | |
| 2006/0004020 A1 | 1/2006 | Jorand-Lebrun et al. | |
| 2007/0037806 A1 | 2/2007 | Schwarz et al. | |
| 2007/0129381 A1 | 6/2007 | Schwarz et al. | |
| 2007/0197794 A1 | 8/2007 | Nadler et al. | |
| 2008/0038342 A1 | 2/2008 | Bergman et al. | |
| 2015/0073032 A1 | 3/2015 | Chollet | |
| 2015/0164859 A1* | 6/2015 | Chollet | A61K 31/401 514/171 |
| 2016/0221944 A1 | 8/2016 | Chollet | |

FOREIGN PATENT DOCUMENTS

| | | |
|---|---|---|
| EP | 2845850 A1 | 3/2015 |
| EP | 2886107 A1 | 6/2015 |
| WO | 02/074741 A2 | 9/2002 |
| WO | 2004/005249 A1 | 1/2004 |
| WO | 2004/076407 A2 | 9/2004 |
| WO | 2005/082848 A2 | 9/2005 |

OTHER PUBLICATIONS

Vrachnis et al. The Oxytocin-Oxytocin Receptor System and Its Antagonists as Tocolytic Agents. International Journal of Endocrinology, 2011, 1-8.*
CAPLUS printout of Pohl et al. Pharmacokinetic interactions of OBE001 and betamethasone in healthy female volunteers. Journal of Clinical Pharmacy and Therapeutics, 2015, 40, 328-332.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Rydzewski, Real World Drug Discovery 2008, 42-43.*
Blockeel, C., et al., "Effects of Barusiban and Atosiban on Frequency of Uterine Contractions in the Luteal Phase after Stimulation: A Randomised Placebo-Controlled Trial," (2009).
Fanchin, Renato, et al., "Uterine Contractions at the Time of Embryo Transfer Alter Pregnancy Rates after In-Vitro Fertilization," vol. 13, No. 7, pp. 1968-1974 (1998).
IsHak, Waguih William, et al., "Male Anorgasmia Treated with Oxytocin," J. Sex Med., pp. 1022-1024 (2008).
Moraloglu, Ozlem, et al., "Treatment with Oxytocin Antagonists before Embryo Transfer May Increase Implantation Rates after IVF," vol. 21, pp. 338-343 (2010).
Pierzynski, Piotr, Oxytocin and Vasopressin V1A Receptors as New Therapeutic Targets in Assisted Reproduction, vol. 22, pp. 9-16 (2011).
Murphy, Michael R., et al., "Changes in Oxytocin and Vasopressin Secretion During Sexual Activity in Men," Journal of Clinical Endocrinology and Metabolism, vol. 65, No. 4, pp. 738-741 (1987).
Visnova, H., et al. Effects of Barusiban, A Selective Oxytocin Antagonist, on Uterine Contractility in the Luteal Phase After Controlled Ovarian Stimulation, pp. 242 (2012).
Clement, P., et al., "Brain Oxytocin Receptors Mediate Ejaculation Elicited by 7-hydroxy-2-(di-N-propylamino) tetralin (7-OH-DPAT) in Anaesthetized Rats," British Journal of Pharmacology, pp. 1150-1159 (2008).
Shinghal, Rajesh MD., et al., "Safety and Efficacy of Epelsiban in the Treatment of Men with Premature Ejaculation: A Randomized, Double-Blind, Placebo-Controlled, Fixed-Dose Study," J Sex Med, pp. 1-12 (2013).
Assinder, S.J., "Oxytocin Increases 5α-Reductase Activity of Human Prostate Epithelial Cells, But Not Stromal Cells," The Prostate 68, pp. 115-121 (2008).
Nicholson, Helen D., "Oxytocin:A Paracrine Regulator of Prostatic Function," Reviews of Reproduction 1, pp. 69-72, (1996).
Saniger, Marcela Arrazola, et al., "Alpha-1-Adrenergic Receptor Blockade Modifies Insulin-Regulated Aminopeptidase (IRAP) Activity in Rat Prostate and Modulates Oxytocin Functions," Drug Metabolism Letters, vol. 5, No. 3, pp. 1-5 (2011).
Assinder, S.J., et al., "Effects of Steroids on Oxytocin Secretion by the Human Prostate in vitro,"International Journal of Andrology, No. 27, pp. 12-18 (2004).

(Continued)

*Primary Examiner* — Matthew Coughlin
*Assistant Examiner* — Po-Chih Chen
(74) *Attorney, Agent, or Firm* — Clark & Elbing LLP; Kristina Bieker-Brady

(57) ABSTRACT

Crystalline (3Z,5S)-5-(hydroxymethyl)-1-[(2'-methyl-1,1-biphenyl-4-yl)carbonyl]pyrrolidin-3-one O-methyloxime is disclosed. A pharmaceutical composition containing the crystalline compound and methods for treating conditions related to the OT-R activity, such as preterm labor, and tor increasing embryo implantation rate in a mammal undergoing embryo transfer, comprising administering the crystalline compound are also disclosed.

5 Claims, 8 Drawing Sheets

(56) References Cited

OTHER PUBLICATIONS

Farina-Lipari, E., et al., "Presence of Atrial Natriuretic Factor in Normal and Hyperplastic Human Prostate and its relationship with Oxytocin Localisation," European Journal of Histochemistry, vol. 47, Issue 2, pp. 133-138, (2003).
Autism Fact Sheet, NINDS, retrieved from the Internet on Jul. 13, 2015 (URL:http://www.ninds.nih.gov/disorders/autism/detail_autism.htm).
M. Caira, "Crystalline Polymophism of Organic Compounds", Topics in Current Chemistry, vol. 198, p. 165-166, Jan. 1998.
Notification of Transmittal of the International Search Report and the Written Opinion of the International Searching Authority for PCT/EP2015/062881, Aug. 5, 2015.
U.S. Appl. No. 15/104,683, filed Jun. 15, 2016, Chollet et al.

\* cited by examiner

CRYSTALLINE (3Z,5S)-5-(HYDROXYMETHYL)-1-[(2'-METHYL-1,1'-BIPHENYL-4-YL)CARBONYL] PYRROLIDIN-3-ONE O-METHYLOXIME, AND METHODS OF USING THE SAME

This application claims the benefit of U.S. Provisional Application No. 62/020,076, filed Jul. 2, 2014. The content of the aforementioned application is incorporated herein by reference in its entirety.

FIELD OF THE INVENTION

The instant disclosure relates to crystalline (3Z,5S)-5-(hydroxymethyl)-1-[(2'-methyl-1,1'-biphenyl-4-yl)carbonyl]pyrrolidin-3-one O-methyloxime and methods of using the same. In addition, the instant disclosure relates to pharmaceutical compositions comprising the crystalline (3Z,5S)-5-(hydroxymethyl)-1-[(2'-methyl-1,1'-biphenyl-4-yl)carbonyl]pyrrolidin-3-one O-methyloxime, methods of making the same and methods of treating conditions related to the OT-R activity, in particular preterm labor, using the crystalline (3Z,5S)-5-(hydroxymethyl)-1-[(2'-methyl-1,1'-biphenyl-4-yl)carbonyl]pyrrolidin-3-one O-methyloxime.

BACKGROUND OF THE INVENTION

Oxytocin (OT) is a cyclic nona-peptide that mediates its physiological actions through activation of the oxytocin receptor (OT-R), a cell membrane receptor belonging to the class of G protein-coupled receptors that is similar to arginine vasopressin receptors. Among other roles in the body, OT causes the contraction of the uterus of mammals during labor. Repeated, concerted and regular contraction of the uterus will cause the dilation of the cervix, the rupture of fetal membranes and lead to expulsion of the fetus. Premature labor is when these contractions occur before the normal term of pregnancy. Preterm increase of uterine activity is the most common expression of preterm labor.

Premature labor leads to undesired premature birth, a serious health problem that remains the major cause of perinatal mortality and severe morbidity, especially respiratory distress syndrome, intraventricular haemorrhage, bronchopulmonary dysplasia and necrotising enterocolitis that are tar more common in preterm than in term infants. Long-term impairments such as cerebral palsy, visual impairment and hearing loss are also more common in preterm infants. Nowadays, preterm birth remains the leading cause of infant mortality and morbidity in industrialized nations. Neonatal intensive care of premature babies is very costly. The actual costs are even higher to society when taking into consideration the healthcare provision of preterm child birth-related ailments, such as respiratory distress syndrome, heart conditions, cerebral palsy, epilepsy, and severe learning disabilities. Thus, managing preterm labor is a significant concern in the field of obstetrics.

The OT/OT-R system plays a vital role in initiating labor in mammals, in particular in humans. The density of OT-R increases markedly in the myometrium before the onset of and during labor. Also, it is thought that the local OT peptide hormone concentration increases significantly before parturition in humans. The high circulating concentrations of progesterone induce uterine quiescence while the uterus acquires contractile ability. Shortly before term, plasma progesterone concentrations fall, OT-R expression in the uterus increases, OT is released and uterine contractile activity increases. At term, the contractions rise to a crescendo, resulting in delivery as a result of two interacting positive feedback loops. The first is a local uterine loop; within the uterus itself contractile prostaglandins are produced and released in response to OT and uterine contractions. These prostaglandins may play a further role in cervical ripening and weakening of fetal membranes. The second loop involves the hypothalamus; in response to uterine contractions and vaginal and cervical distension, monocellular oxytocin neurons in the hypothalamus increase their activity resulting in the release of OT from their axon terminals in the posterior pituitary. The released OT acts upon the uterus both to stimulate the further production of prostaglandins and to contribute further to the contractions of the uterus.

Another potential benefit of antagonizing OT-R is in the field of Assisted Reproductive Technology (ART), Although many efforts have been made to improve the results of assisted reproduction over the last decades, the overall effectiveness of in vitro fertilization (IVF) technique still remains limited. A variety of factors can influence success rates after IVF. Transfer of the embryo is an important factor influencing the outcome of the fertility treatment. ART consists first in performing a controlled ovarian hyperstimulation (COH) for stimulating the growth of several follicles, allowing retrieval of several oocytes for IVF. COH is associated with supra-physiological estradiol levels and it has been shown that uterine contractile activity is increased in IVF patients at the time of embryo transfer as compared with a spontaneous menstrual cycle.

Uterine contractions constitute one of the most fundamental components of uterine receptivity, because contractile activity of the uterus plays an important role in embryo implantation. Excessive uterine contractions may decrease the embryo implantation rate in an IVF cycle because contractile activity might expel embryos from the uterus. To date, treatment strategies used to reduce uterine contractions before embryo transfer, such as the use of beta agonists or non-steroid anti-inflammatory drugs, have not provided sufficient benefit In addition, systemic and endometrial levels of OT, as well as OT-R expression, are strongly influenced by estradiol, e.g., in non-pregnant women, the highest level of expression of OT-R is observed at mid-menstrual cycle and in pregnant women near term.

For at least these reasons, it is believed that reducing uterus contractions at the time of embryo transfer by the administration of an OT-R and/or V1a antagonist may increase embryo implantation rate and thus pregnancy rate in ART.

Thus, blocking the effect of OT by antagonizing OT-R might represents an attractive modality tor the treatment of diseases related to the OT-R activity, in particular preterm labor and embryo implantation failure due to uterine contractions.

Tocolytics, i.e. uterus relaxing agents, have been used in clinical studies for the pharmaceutical treatment of preterm labor. Most of these agents are used oil-label. They have shown very limited efficacy, if any, in prolonging gestation and have not shown any clear demonstration of improvement of neonate outcome. In addition, many tocolytics are often associated with unwanted adverse effects on women, fetus or neonate. Such tocolytics include beta-2-adrenergic agonists, prostaglandin synthesis inhibitors, magnesium sulfate, nitric acid donors and calcium channel blockers. Beta-2-adrenergic agonists such as ritodrine or terbutaline cause a number of cardiovascular and metabolic side effects including maternal tachycardia, palpitations, hypotension, altered thyroid function and fetal and neonatal hypoglycemia, tachycardia.

The calcium channel blocker nifedipine is also used to try to stop contractions. Some of the possible side effects from this medicine include facial flushing, headache, nausea, palpitations, and lightheadedness. The total prostaglandin synthesis inhibitor (NSAID) indomethacin has also been used, but it can also have serious effects on the fetus, e.g., constriction of ductus arteriosus, pulmonary hypertension, decrease in renal function with oligohydramnios, intraventricular hemorrhage, hyperbilirubinemia, necrotizing enterocolitis, and also side effects tor the mother, e.g., abdominal discomfort, nausea, vomiting, depression and dizzy spells. Sulindac, another NSAID, has a side effect profile similar to indomethacin. Meta-analyses conducted on magnesium sulfate have failed to support it as a tocolytic. Women reported side effects such as flushing, lethargy, headache, muscle weakness, pulmonary edema and cardiac arrest. Further, a newborn who has been exposed to magnesium sulfate may exhibit lethargy, hypotonia, respiratory depression, bone problems, osteopenia and fractures. The FDA is now advising healthcare professionals against using magnesium sulfate injection for longer than 5-7 days to stop preterm labor in women.

Another pharmaceutical, atosiban, a dual vasopressin V1a receptor and OT-R antagonist, is marketed in the EU and is used to stop contractions and delay preterm delivery by a few days. Atosiban is a peptide that is not orally bioavailable and must be administered parenterally. It degrades rapidly in circulation by enzymes and its use is limited to a maximum of 48 hours.

Orally active small molecule antagonists that are selective for the OT-R have been developed in an attempt to overcome these problems. Specifically. Non-peptide OT-R antagonists were developed such as pyrrolidine derivatives (WO 01/72705, WO 02/102799, WO 2002/07474, WO 2004/005249).

Pyrrolidine derivatives, as mixtures of isomers, arc disclosed for use as oxytocin antagonists in WO 2004/005249. No suitable conditions of crystallization of pure (3Z,5S)-5-(hydroxymethyl)-1-[(2'-methyl-1,1-biphenyl-4-yl)carbonyl] pyrrolidin-3-one O-methyloxime or of the crude isomeric mixture were reported therein.

There remain significant unmet needs for efficient and orally selective OT-R antagonist for the treatment of diseases related to the OT-R activity, in particular preterm labor, in particular, there is a need for an orally administrable pharmaceutically effective product, which is rapidly absorbed, has a half-life long enough to support once daily administration, and is safe for mother and fetus in a prolonged maintenance treatment over several weeks until the pregnancy comes to term.

SUMMARY OF THE INVENTION

An embodiment is directed to crystalline (3Z,5S)-5-(hydroxymethyl)-1-[(2'-methyl-1,1-biphenyl-4-yl)carbonyl] pyrrolidin-3-one O-methyloxime. In embodiments thereof the crystalline compound may have an XRPD pattern substantially as illustrated in FIG. 1, a DSC curve substantially as illustrated in FIG. 6 or FIG. 7, or a TGA curve substantially as illustrated, in FIG. 8 or FIG. 9.

Another embodiment is a pharmaceutical composition comprising crystalline (3Z,5S)-5-(hydroxymethyl)-1-[(2'-methyl-1,1'-biphenyl-4-yl)carbonyl]pyrrolidin-3-one O-methyloxime and a pharmaceutically acceptable excipient. Yet another embodiment is a method for treating a condition related to the OT-R activity, comprising administering to a subject a therapeutically effective amount of crystalline (3Z,5S)-5-(hydroxymethyl)-1-[(2'-methyl-1,1'-biphenyl-4-yl)carbonyl]pyrrolidin-3-one O-methyloxime. The condition related to the OT-R activity may be selected from the group consisting of preterm labor, premature birth, dysmenorrhea, premature ejaculation, sexual dysfunction, endometriosis, embryo implantation failure due to uterine contractions, infertility, benign prostatic hyperplasia, neuropsychiatric disorders, autism, social behavior disorders, psycho-social stress, and cardiovascular disorders.

DETAILED DESCRIPTION OF THE INVENTION

Crystalline Form

Figure 1:
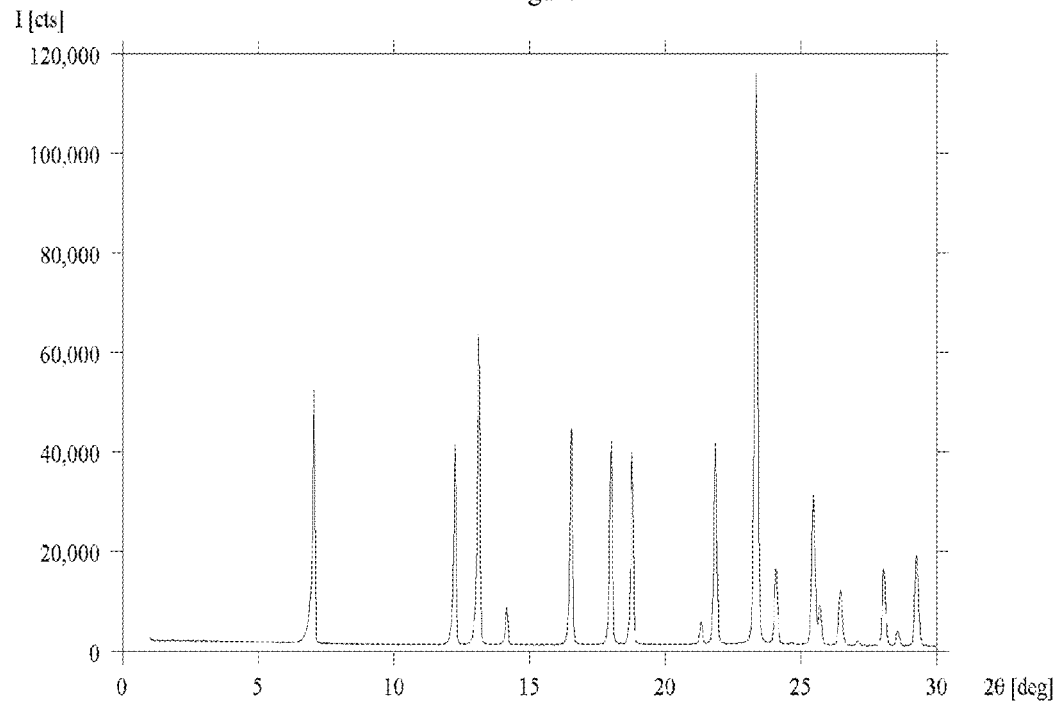
FIG. 1 shows X-ray powder diffraction (XRPD) analysis for crystalline (3Z,5S)-5-(hydroxymethyl)-1-[(2'-methyl-1,1'-biphenyl-4-yl)carbonyl]pyrrolidin-3-one O-methyloxime after synthesis.

Novel crystalline (3Z,5S)-5-(hydroxymethyl)-1-[(2'-methyl-1,1-biphenyl-4-yl)carbonyl]pyrrolidin-3-one O-methyloxime is disclosed herein. Initial attempts to crystallize (3Z,5S)-5-(hydroxymethyl)-1-[(2'-methyl-1,1'-biphenyl-4-yl)carbonyl]pyrrolidin-3-one O-methyloxime failed. Later, over 120 polymorph screen experiments were performed. More than half did not produce solid material suitable for further characterization and approximately one-third produced the amorphous form. After much experimentation and discovery, the inventors obtained a stable crystalline form of (3Z,5S)-5-(hydroxymethyl)-1-[(2'-methyl-1,1'-biphenyl-4-yl)carbonyl]pyrrolidin-3-one O-methyloxime, which may be used as a pharmaceutical active ingredient in a pharmaceutical composition. The present disclosure teaches how to make this novel crystalline form and the benefits of it.

An embodiment of the present invention is crystalline (3Z,5S)-5-(hydroxymethyl)-1-[(2'-methyl-1,1'-biphenyl-4-yl)carbonyl]pyrrolidin-3-one O-methyloxime.

The crystalline compound of this invention is a substantially pure crystalline compound. A substantially pure crystalline compound is predominantly made up of a single crystalline phase, preferably over about 85% by weight is made up of the single crystalline phase, more preferably over about 90%, more preferably over about 95%, still more preferably over about 98% and most preferably about 100%. In another embodiment, the crystalline compound is substantially free of amorphous (3Z,5S)-5-(hydroxymethyl)-1-[(2'-methyl-1,1'-biphenyl-4-yl)carbonyl]pyrrolidin-3-one O-methyloxime. Preferably, less than about 8% by weight of the amorphous form is present, more preferably, less than about 5% by weight of amorphous form is present, and still more preferably, less than about 3% by weight of amorphous form is present.

The term "crystalline" as used herein refers to compounds in a solid state having a periodic and repeating three-dimensional internal arrangement of atoms, ions or molecules characteristic of crystals. The term crystalline does not necessarily mean that the compound has the visual appearance of crystals to the naked eye, but that it has this crystal-like internal structural arrangement. The term "amorphous" as used herein refers to compounds lacking a crystalline structure: no repeating pattern, only short range order, extensively disordered.

Crystalline (3Z,5S)-5-(hydroxymethyl)-1-[(2'-methyl-1,1'-biphenyl-4-yl)carbonyl]pyrrolidin-3-one O-methyloxime may be made using the following solvents: diethyl ether (also referred to as ethyl ether) or ethyl acetate, and preferably using diethyl ether. In a certain embodiment of the invention, the amount of residual diethyl ether present after crystallization is less than about 6% by weight, preferably less than about 4% by weight, and more preferably less than about 2% by weight. To reduce the amount of residual diethyl ether in with the crystalline compound and yet avoid melting the solid, the solid may be vacuum-dried at a temperature between about 35°C and about 60°C, preferably between about 40× and about 55° C., more preferably between about 40*C and about 50°C., and most preferably at about 45° C., tor over a period of at least about 50 hours, preferably, at least about 100 hours, and more preferably, for at least about 130 hours. In a certain embodiment, crystalline (3Z,5S)-5-(hydroxymethyl)-1-[(2'-methyl-1,1'-biphenyl-4-yl)carbonyl]pyrrolidin-3-one O-methyloxime is prepared using diethyl ether crystallization and the resulting solid is vacuum-dried at about 45° C. for about 133 hours to remove the residual ether. Preferably, little manipulation of the solid is needed to aid in drying.

Crystalline (3Z,5S)-5-(hydroxymethyl)-1-[(2'-methyl-1,1'-biphenyl-4-yl)carbonyl]pyrrolidin-3-one O-methyloxime may be used to treat, prevent, or otherwise ameliorate conditions related to the OT-R activity.

Conditions related to the OT-R activity Include preterm labor, premature birds, dysmenorrhea, premature ejaculation, sexual dysfunction, endometriosis, embryo implantation failure due to uterine contractions, infertility, benign prostatic hyperplasia, neuro-psychiatric disorders, autism, social behavior disorders, psycho-social stress, and cardiovascular disorders.

The term "preterm labors" referring also to premature labor, shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" refers to a condition characterized by cyclic pain associated with menses during ovulatory cycles. The pain is thought to result from uterine contractions and ischemia.

The term "sexual dysfunction" refers to any disturbance or variation in the four phases—excitement phase, plateau phase, orgasmic phase and resolution phase characterizing the human sexual response.

The term "neuro-psychiatric disorders" as used herein refers to mental disorders attributable to diseases of the nervous system, e.g. depression, obsessive-compulsive disorder and others.

The term "social behavior disorders" as used herein refers to emotional disturbance, inappropriate types of behavior or feelings, pervasive mood of unhappiness or depression and a range of perceived difficulties to build or maintain satisfactory interpersonal relationships The term "psycho-social stress" as used herein refers to a condition resulting front a perceived threat to the social status, social esteem, self-worth, respect or acceptance within a group, and that lead to development of a stress response in the body and physical symptoms.

As for its use in embryo implantation, infertility, which affects about 10% of human pairs worldwide, may be treated by in vitro fertilization and embryo transfer (IVF-ET) or in less complicated eases, by artificial insemination. Generally, a success of an embryo transfer is dependant on uterine receptivity, an entity that is defined as an ability of uterus to provide optimal conditions mandating proper implantation and embryo development, Basic components of uterine receptivity are uterine contractile activity and the condition of endometrium. Uterine contractions occurring during the embryo transfer may expel embryos from the uterus towards vagina or oviducts, which may be a cause of unsuccessful treatment, or in latter case a cause of extrauterine pregnancy, a serious, potentially life-threatening complication. Thus, the crystalline compound may be used to assist reproduction, and more particularly for use by reducing embryo implantation failure due to uterine contractions.

General methods for analyzing crystalline forms include crystal analysis by X-ray powder diffraction (XRPD), differential scanning calorimetry (DSC) and thermo-gravimetric analysis (TGA).

XRPD analysis as disclosed herein was collected on an fuel XRG-3000 Diffractometer or a PANalytical X'Pert PRO MPD diffractometer.

The IneI XRG-3000 diffractometer was equipped with a curved position-sensitive detector with a 2θ range of 120°. Real time data was collected using Cu Kα radiation starting a approximately 4°2θ at a resolution of 0.03°2θ. The tube voltage and amperage were set to 40 kV and 30 mA, respectively. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard. This machine was used in collecting the XRPD pattern shown as the top line in FIG. 2, i.e., for the crystalline compound made by ethyl acetate crystallization.

The PANalytical X'Pert PRO MPD diffractometer was used either with an incident beam of Cu Kα radiation produced using a long, fine-focus source and a nickel filter, or with an incident beam of Cu radiation produced using an Optix long, fine-focus source.

In the former case of using an incident beam of Cu Kα radiation produced using a long, fine-focus source and a nickel filter, the diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on s silicon zero-background substrate or packed in a backfill holder, Antiscatter slits (SS) were used to minimize the background generated by air, Sofler slits for the incident and diffracted beams were used to minimize broadening from axial divergence. Diffraction patterns were collected using a scanning position-sensitive detector (X'Celerator) located 240 mm from the sample and Data Collector software v.2.2b. The data acquisition parameters for each pattern were displayed above the image in the Data section including the divergence slit (DS) and the incident-beam (SS). This machine was used in collecting the XRPD pattern shown as the bottom line in FIG. 2, i.e., for the crystalline compound made by diethyl ether crystallization on a small-scale, vacuum-dried at ambient temperature for 20 hours and further vacuum-dried at 45° C. for 65 hours.

In the latter case of using an incident beam of Cu radiation produced using an Optix long, fine-focus source, an elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v.2.2b. The data acquisition parameters for each pattern were displayed above the image in the Data section including the divergence slit (DS) before the mirror. This machine was used in collecting the XRPD patterns shown in FIGS. 1, 3, 4, 5 and the middle line in FIG. 2.

Figure 3:
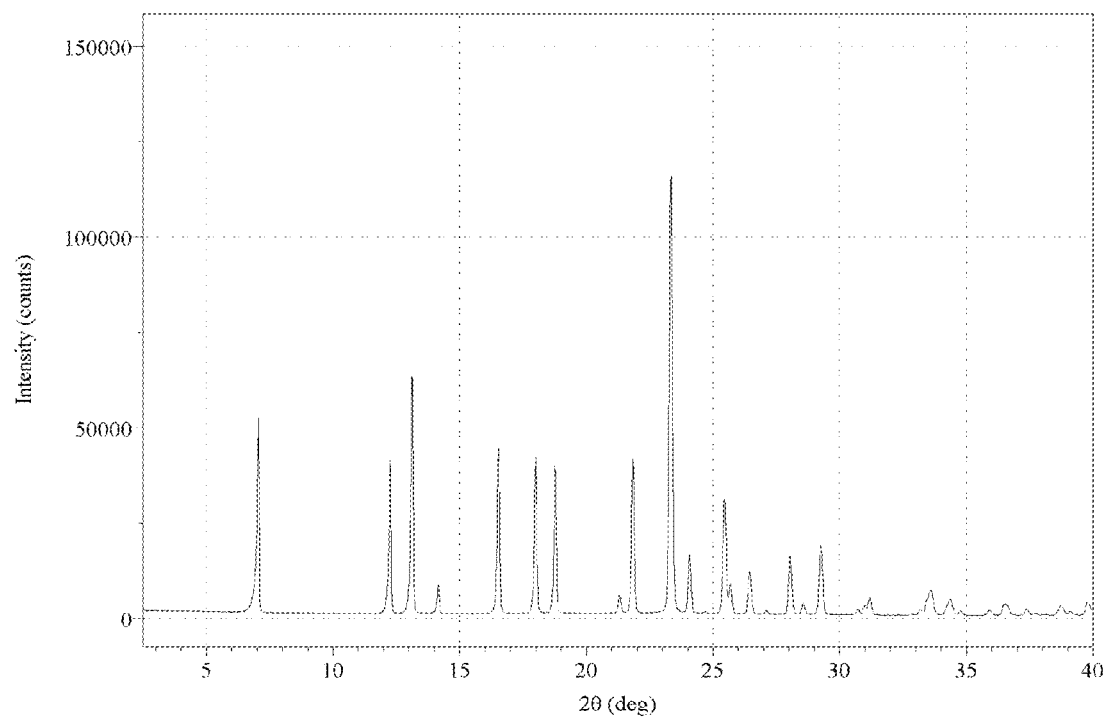
FIG. 3 shows the observed peaks for crystalline (3Z,5S)-5-(hydroxymethyl)-1-[(2'-methyl-1,1'-biphenyl-4-yl)carbonyl]pyrrolidin-3-one O-methyloxime prepared by small-scale diethyl ether crystallization, vacuum-dried at ambient temperature for 20 hours, output rendered using Triads™v2.0.

In certain embodiments, crystalline (3Z,5S)-5-(hydroxymethyl)-1-[(2'-methyl-1,1'-biphenyl-4-yl)carbonyl]pyrrolidin-3-one O-methyloxime has an XRPD pattern substantially as illustrated in FIG. 1 after crystallization. In another embodiment, crystalline (3Z,5S)-5-(hydroxymethyl)-1-[(2'-methyl-1,1'-biphenyl-4-yl)carbonyl]pyrrolidin-3-one O-methyloxime has an XRPD pattern substantially as illustrated in FIG. 3.

The term "XRPD pattern" as used herein refers to the graphical representation of the data collected by XRPD analysis. XRPD analysis is a technique used to characterize the crystallographic structure, size, and preferred orientation in polycrystalline or powdered solid samples. This diffraction is also used to characterize heterogeneous solid mixtures to determine the percent of crystalline compounds present and can provide structural information on unknown materials.

The terms "substantially" and "about" as used herein in reference to an XPRD pattern refer to the XPRD pattern wherein a listed peak(s) appears within 0.2 degrees 2-theta, including within 0.1 degrees 2-theta of a given 2-theta value.

Figure 2:
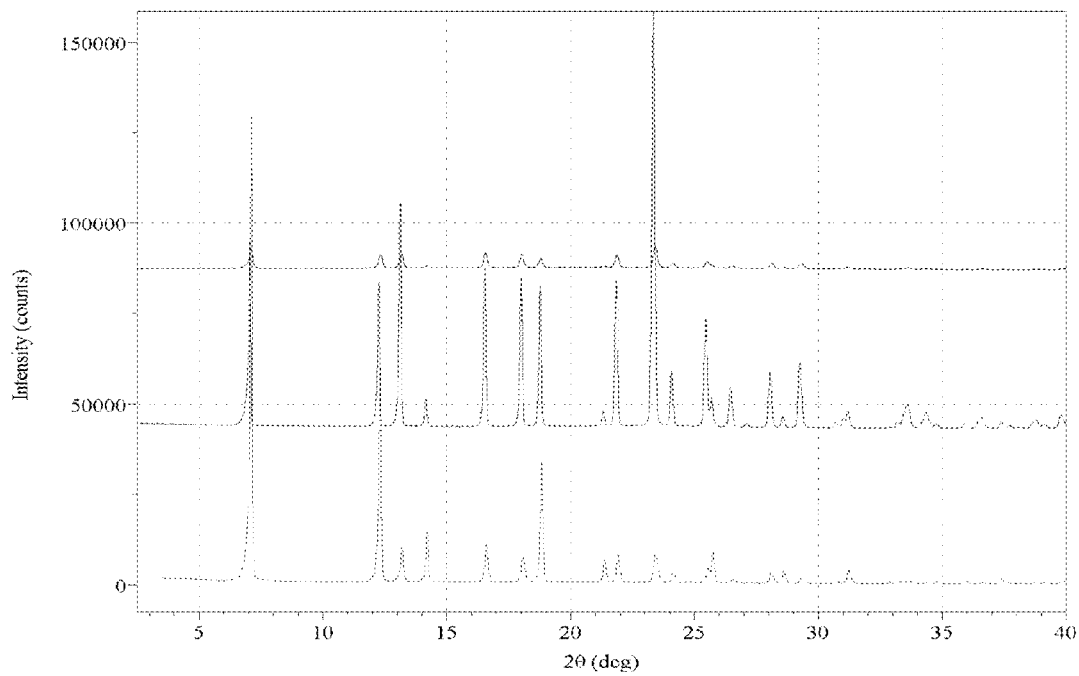
FIG. 2 shows comparative XRPD analysis for: crystalline (3Z,5S)-5-(hydroxymethyl)-1-[(2'-methyl-1,1'-biphenyl-4-yl)carbonyl]pyrrolidin-3-one O-methyloxime prepared by ethyl acetate crystallization (top line); crystalline (3Z,5S)-5-(hydroxymethyl)-1-[(2'-methyl-1,1'-biphenyl-4-yl)carbonyl]pyrrolidin-3-one O-methyloxime prepared by diethyl ether crystallization on a small-scale, vacuum-dried at ambient temperature for 20 hours (middle line): and crystalline (3Z,5S)-5-(hydroxymethyl)-1-[(2'-methyl-1,1'-biphenyl-4-yl)carbonyl]pyrrolidin-3-one O-methyloxime prepared by diethyl ether crystallization on a small-scale, vacuum-dried at ambient temperature for 20 hours and further vacuum-dried at 45° C. for 65 hours (bottom line).

"After crystallization" means after preparation of the solid and drying at ambient temperature to about 45° C. For example, as shown in FIG. 2, the XRPD patterns are the same for a sample dried at ambient temperature for about 20 hours and a sample further vacuum-dried at about 45° C. for about 65 hours. Thus, vacuum-drying at about 45° C. for about 65 hours does not change the solid form of crystalline (3Z,5S)-5-(hydroxymethyl)-1-[(2'-methyl-1,1'-biphenyl-4-yl)carbonyl]pyrrolidin-3-one O-methyloxime.

In a preferred embodiment, crystalline (3Z,5S)-5-(hydroxymethyl)-1-[(2'-methyl-1,1'-biphenyl-4-yl)carbonyl]pyrrolidin-3-one O-methyloxime has characteristic peaks at diffraction angle 2-theta degrees appearing at least at about 7.05, about 13.13 and about 23.34, as measured by XRPD, In a more preferred embodiment, crystalline (3Z,5S)-5-(hydroxymethyl)-1-[(2'-methyl-1,1'-biphenyl-4-yl)carbonyl]pyrrolidin-3-one O-methyloxime has characteristic peaks at diffraction angle 2-theta degrees appearing at least at about 7.05, about 13.13, about 16.54, about 21.84, and about 23.34, as measured by XRPD, and still more preferable, characteristic peaks at diffraction angle 2-theta degrees appearing at least at about 7.05, about 12.25, about 13.13, about 16.54, about 18.00, about 21.84, and about 23.34, as measured by XRPD.

The term "characteristic peak" as used herein refers to a peak in the XRPD pattern having an intensity at least 20%, preferably 30% greater than the baseline noise.

In another embodiment, crystalline (3Z,5S)-5-(hydroxymethyl)-1-[(2'-methyl-1,1'-biphenyl-4-yl)carbonyl]pyrrolidin-3-one O-methyloxime has peaks as set forth in Table 1, as measured by XRPD, and as shown, for example, in FIG. 3.

TABLE 1

Observed peaks by XRPD analysis.

| °2θ | d space (Å) | Intensity (%) |
|---|---|---|
| 7.05 ± 0.20 | 12.520 ± 0.354 | 45 |
| 12.25 ± 0.20 | 7.218 ± 0.117 | 36 |
| 13.13 ± 0.20 | 6.739 ± 0.102 | 55 |
| 14.16 ± 0.20 | 6.250 ± 0.088 | 8 |
| 16.54 ± 0.20 | 5.356 ± 0.064 | 38 |
| 18.00 ± 0.20 | 4.923 ± 0.054 | 36 |

TABLE 1-continued

Observed peaks by XRPD analysis.

| °2θ | d space (Å) | Intensity (%) |
|---|---|---|
| 18.77 ± 0.20 | 4.723 ± 0.050 | 34 |
| 21.32 ± 0.20 | 4.165 ± 0.039 | 5 |
| 21.84 ± 0.20 | 4.066 ± 0.037 | 36 |
| 23.34 ± 0.20 | 3.808 ± 0.032 | 100 |
| 24.08 ± 0.20 | 3.693 ± 0.030 | 14 |
| 24.67 ± 0.20 | 3.605 ± 0.029 | 1 |
| 25.45 ± 0.20 | 3.497 ± 0.027 | 27 |
| 25.69 ± 0.20 | 3.465 ± 0.027 | 8 |
| 26.45 ± 0.20 | 3.367 ± 0.025 | 10 |
| 27.09 ± 0.20 | 3.289 ± 0.024 | 2 |
| 28.05 ± 0.20 | 3.179 ± 0.022 | 14 |
| 28.56 ± 0.20 | 3.123 ± 0.021 | 3 |
| 29.26 ± 0.20 | 3.050 ± 0.020 | 16 |
| 30.72 ± 0.20 | 2.908 ± 0.018 | 2 |
| 31.00 ± 0.20 | 2.882 ± 0.018 | 3 |
| 31.19 ± 0.20 | 2.865 ± 0.018 | 5 |
| 33.19 ± 0.20 | 2.697 ± 0.016 | 2 |
| 33.60 ± 0.20 | 2.665 ± 0.015 | 6 |
| 34.36 ± 0.20 | 2.608 ± 0.015 | 4 |
| 34.75 ± 0.20 | 2.580 ± 0.014 | 2 |
| 35.91 ± 0.20 | 2.499 ± 0.013 | 2 |
| 36.52 ± 0.20 | 2.458 ± 0.013 | 3 |
| 37.38 ± 0.20 | 2.404 ± 0.012 | 2 |
| 37.70 ± 0.20 | 2.384 ± 0.012 | 1 |
| 38.73 ± 0.20 | 2.323 ± 0.012 | 3 |
| 39.11 ± 0.20 | 2.301 ± 0.011 | 2 |
| 39.80 ± 0.20 | 2.263 ± 0.011 | 4 |

TGA and DSC analysis are used to measure thermal behavior and can be used to distinguish polymorphs. One polymorphic form may exhibit thermal behavior different from that of the amorphous material or another polymorphic form.

DSC is a thermoanalytical technique in which the difference in the amount of heat required to increase the temperature of a sample and reference is measured as a function of temperature. DSC can be used to measure a number of characteristic properties of a sample, allowing observation of crystallization events. Specifically, with DSC, it is possible to observe small energy changes that occur as matter transitions from a solid to a liquid crystal and from a liquid crystal to an isotropic liquid. The presence of events in the DSC curve can be used to assess the compound's stability, as well as the presence of solvates or hydrates.

DSC analysts as disclosed herein was collected on a TA Instruments differential scanning calorimeter 2920, The instrument was calibrated for energy And temperature using indium. The sample was placed into a standard aluminum DSC pan with a non-crimped lid configuration, and the weight accurately Recorded. The sample cell was equilibrated at 25° C. and heated under a nitrogen Purge at a rate of 10° C./min, up to a final temperature of 350° C. Samples Prepared for glass transition determination were heated at 20° C./min in a cycling Experiment. The cycling experiments consisted of heating the material to either 120° C. or 145° C., cooling it to 10° C., heating it back up to the temperature again, Cooling it to 10° C., and then heating it to a final temperature of 350° C.

TGA is used to determine changes in weight in relation to change in Temperature, which may reveal degradation of the compound and the presence of Solvates or hydrates. TGA analysis as disclosed herein was collected on a TA Instruments 2050 thermogravimetric analyzer. The temperature was calibrated Using Alumel™ and Nickel. Each sample was placed in a platinum pan and Inserted into the TG furnace. The furnace was heated under a nitrogen purge. The data acquisition parameters were displayed for each thermogram. The Sample having the TGA curve shown in FIG. 8 was heated from ambient Temperature to 350° C., at 10° C./min. The sample having the TGA curve shown in FIG. 9 was first equilibrated at 25° C., then headed to 350° C., at 10° C./min.

Figure 6:
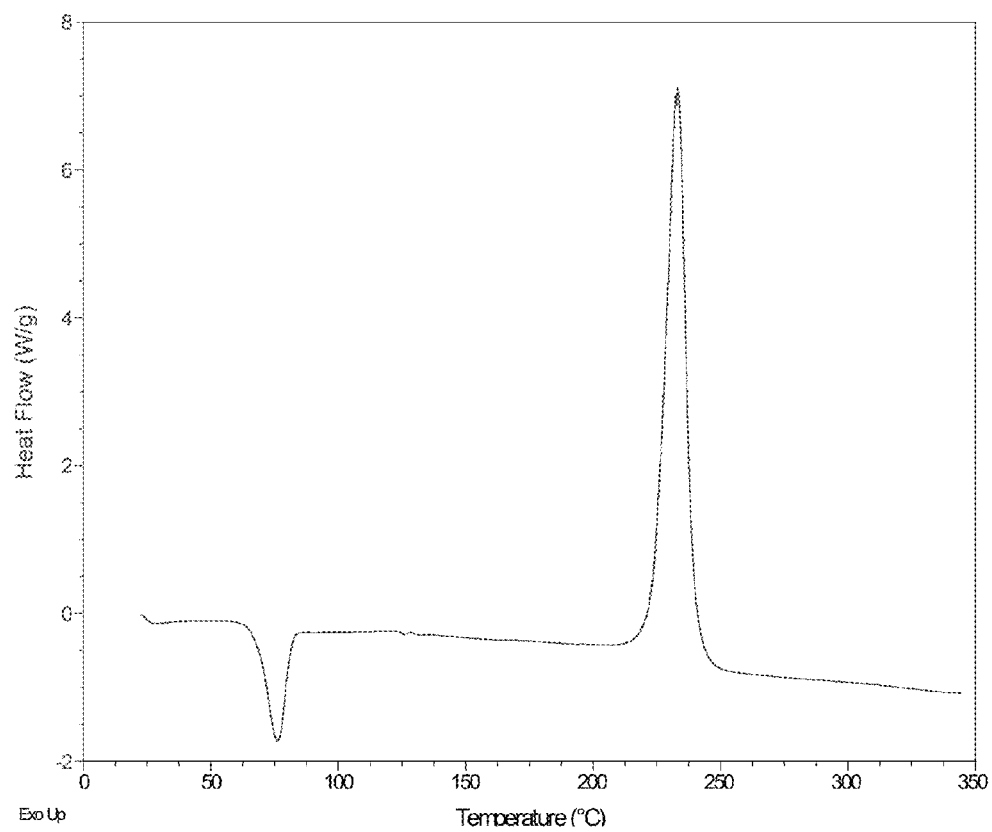
FIG. 6 is a differential scanning calorimetry (DSC) curve of crystalline (3Z,5S)-5-(hydroxymethyl)-1-[(2'-methyl-1,1-biphenyl-4-yl)carbonyl]pyrrolidin-3-one O-methyloxime prepared by crystallization from diethyl ether.
Figure 7:
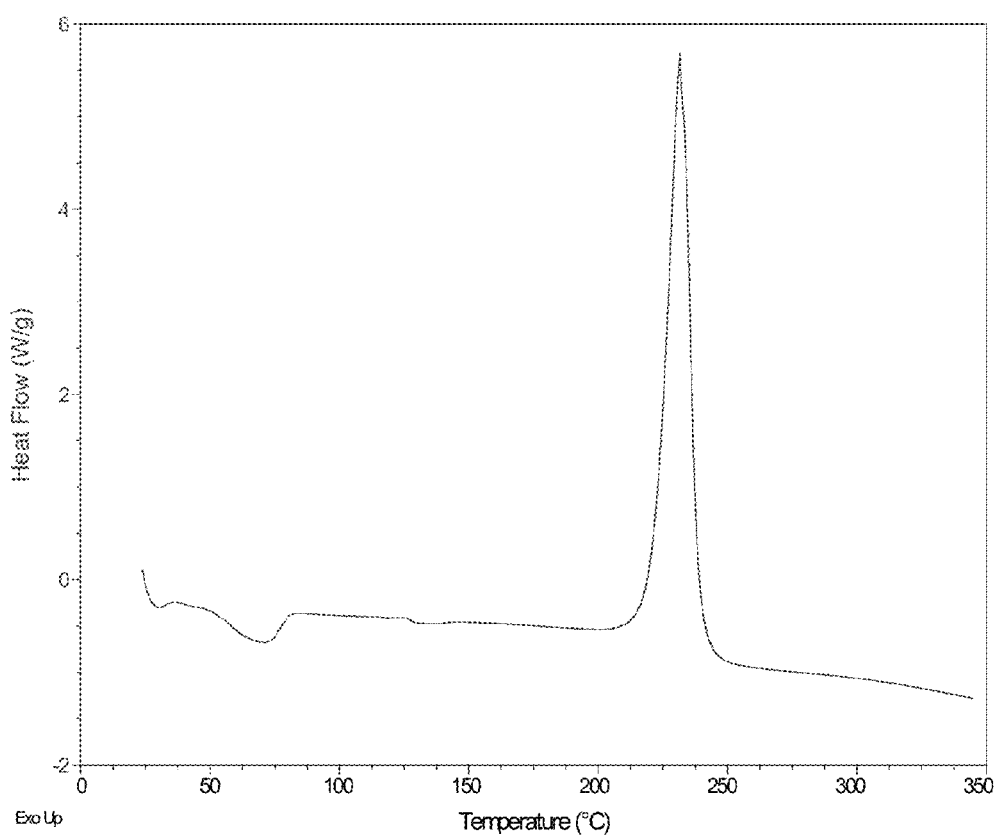
FIG. 7 is a DSC curve of crystalline (3Z,5S)-5-(hydroxymethyl)-1-[(2'-methyl-1,1-biphenyl-4-yl)carbonyl] pyrrolidin-3-one O-methyloxime prepared by crystallization from ethyl acetate.

In a certain embodiment, crystalline (3Z,5S)-5-(hydroxymethyl)-1-[(2'-methyl-1,1'-biphenyl-4-yl)carbonyl]pyrrolidin-3-one O-methyloxime exhibits a DSC curve substantially as illustrated in FIG. 6 or FIG. 7. In another embodiment, crystalline (3Z,5S)-5-(hydroxymethyl)-1-[(2'-methyl-1,1'-biphenyl-4-yl)carbonyl]pyrrolidin-3-one O-methyloxime exhibits a DSC curve with an endotherm with a signal maximum around about 70° C. to about 77° C., a baseline shift at about 122° C. to about 130° C. and a large exotherm with a signal maximum of about 230° C. to 235° C., which is most likely due to decomposition. Crystalline (3Z,5S)-5-(hydroxymethyl)-1-[(2'-methyl-1,1'-biphenyl-4-yl)carbonyl]pyrrolidin-3-one O-methyloxime prepared using ethyl acetate may exhibit a DSC curve with a small, broad endotherm with a signal maximum between about 71° C. and about 72° C., preferably at about 71.67° C., a baseline shift between about 126° C. and About 127° C., preferably about 127.46° C., and a large exotherm with a signal maximum between about 231° C. and about 232° C., preferably at about 231.50° C. Crystalline (3Z,5S)-5-(hydroxymethyl)-1-[(2'-methyl-1,1'-biphenyl-4-yl)carbonyl]pyrrolidin-3-one O-methyloxime prepared using diethyl ether may exhibit a DSC curve with an endotherm with a signal maximum at about 76° C., a baseline shift at about 124° C. to, and a large exotherm with a signal maximum of about 233° C.

The term "substantially," as used herein in reference to DSC curve means the DSC curve demonstrating a peak(s) within 1° C., including within 0.5° C. of a given temperature.

Figure 8:
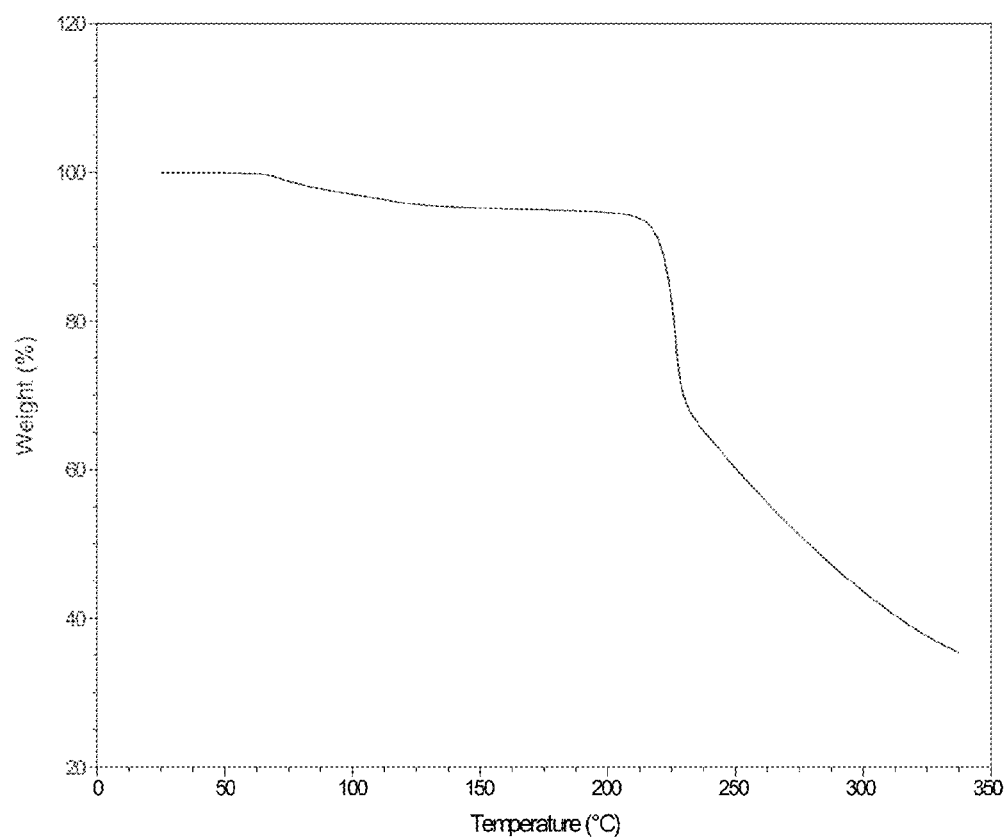
FIG. 8 is a thermo-gravimetric analysis (TGA) curve of crystalline (3Z,5S)-5-(hydroxymethyl)-1-[(2'-methyl-1,1'-biphenyl-4-yl)carbonyl]pyrrolidin-3-one O-methyloxime prepared by crystallization from diethyl ether on a small-scale.
Figure 9:
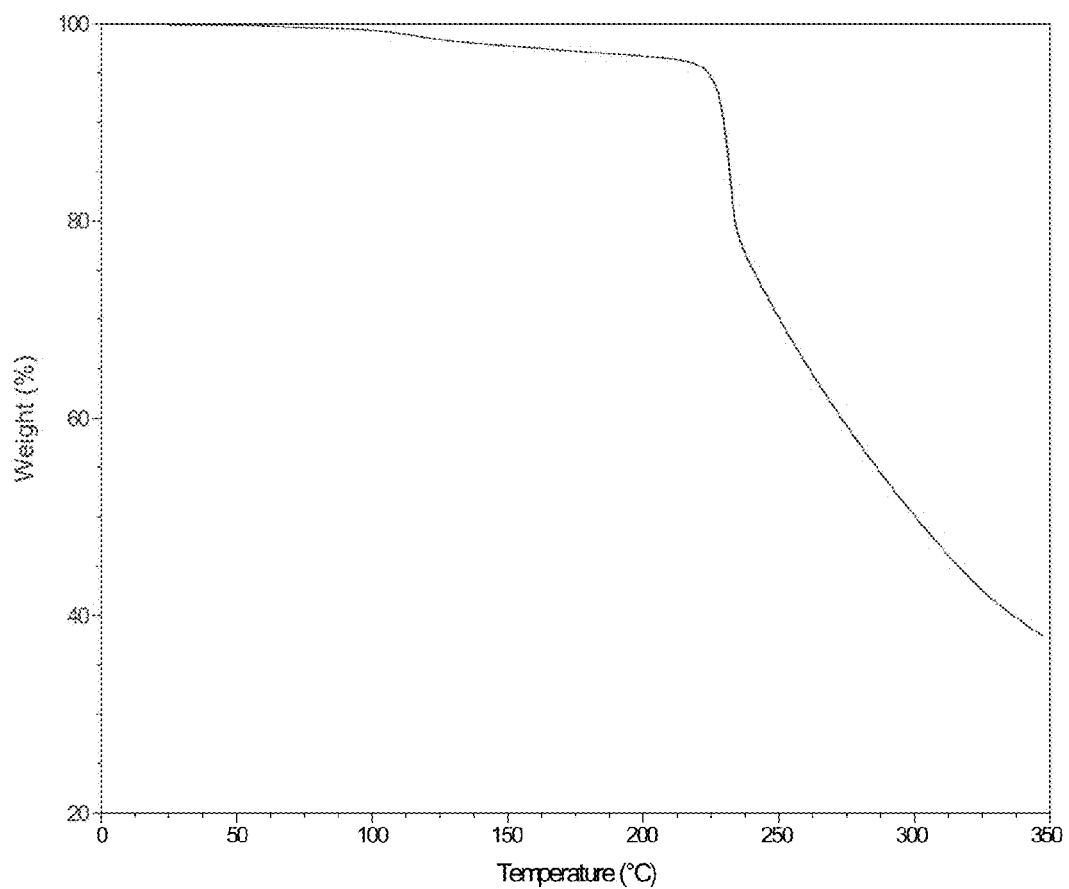
FIG. 9 is a TGA curve of crystalline (3Z,5S)-5-(hydroxymethyl)-1-[(2'-methyl-1,1-biphenyl-4-yl)carbonyl]pyrrolidin-3-one O-methyloxime prepared by crystallization from ethyl acetate.

In a certain embodiment, crystalline (3Z,5S)-5-(hydroxymethyl)-1-[(2'-methyl-1,1'-biphenyl-4-yl)carbonyl]pyrrolidin-3-one O-methyloxime exhibits a TGA curve substantially as illustrated in FIG. 8 or FIG. 9. Preferably, crystalline (3Z,5S)-5-(hydroxymethyl)-1-[(2'-methyl-1,1'-biphenyl-4-yl)carbonyl]pyrrolidin-3-one O-methyloxime analyzed by TGA exhibits a weight loss of about 2% to about 7% from about 25° C. to about 200° C., and, more preferably, a weight loss of about 3% to about 6% from about 25° C. to about 200° C. In a certain embodiment, alter crystallization using diethyl ether, crystalline (3Z,5S)-5-(hydroxymethyl)-1-[(2'-methyl-1,1'-biphenyl-4-yl)carbonyl]pyrrolidin-3-one O-methyloxime analyzed by PGA exhibits a weight loss of about 4.5% to about 5.8%, more preferably about 5.1% to about 5.6%. from about 25° C. to about 200° C.

The term "substantially," as used herein in reference to the TGA curve means the curve demonstrating a percent weight loss within 1%. including within 0.5% of a given value in relation to temperature change.

In another embodiment, crystalline (3Z,5S)-5-(hydroxymethyl)-1-[(2'-methyl-1,1'-biphenyl-4-yl)carbonyl]pyrrolidin-3-one O-methyloxime formulated in a tablet or a capsule is stable during storage for at least 6 months at about 25° C. and about 60% relative humidity, preferably, for at least 12 months at about 25° C. and about 60% relative humidity, and more preferably for at least 12 months at about 2° C. to about 8° C. and ambient humidity. As used herein, stability during storage means at least 95% of the crystalline compound is unchanged from the start of the storage period, preferably at least 96% of the crystalline compound is unchanged from the start of the storage period, most preferably at least 97% of the crystalline compound is unchanged from the start of the storage period, The term "stable" and "stability" as used herein refers to both the physical form and the chemical purity of the crystalline compound. "The crystalline compound" as used herein refers to the disclosed crystalline (3Z,5S)-5-(hydroxymethyl)-1-[(2'-methyl-1,1'-biphenyl-4-yl)carbonyl]pyrrolidin-3-one O-methyloxime of the present invention. Physical stability may be measured by XPRD.

Ambient conditions, as used herein, means a temperature of about 20° C. to about 25° C. and a relative humidity (RH) of about 40%.

Pharmaceutical Compositions

One embodiment of the invention is directed to a pharmaceutical composition comprising crystalline (3Z,5S)-5-(hydroxymethyl)-1-[(2'-methyl-1,1'-biphenyl-4-yl)carbonyl]pyrrolidin-3-one O-methyloxime and a pharmaceutically acceptable excipient.

The pharmaceutical composition of the present invention comprises an effective amount of the crystalline compound, a pharmaceutically acceptable excipient, and, in some embodiments, if may also contain one or more additional active ingredients. The content of crystalline compound in the pharmaceutical composition of the present invention varies depending on the subject of administration, route of administration and target disease, among other variables. The pharmaceutical composition of the present invention may be administered orally, topically (e.g., transdermal etc.), vaginally, rectally, or parenterally (e.g., intravenous, etc). In an embodiment, the pharmaceutical composition is administered orally.

Examples of topical administration of the pharmaceutical composition include transdermal, buccal or sublingual application. For topical applications, the pharmaceutical composition can be suitably admixed in a pharmacologically inert topical carrier, such as a gel an ointment, a lotion or a cream. Such pharmacologically inert topical carriers include water, glycerol alcohol, propylene glycol, fatty alcohols, triglycerides, fatty acid esters, or mineral oils. Other possible pharmacologically inert topical carriers are liquid petrolatum, isopropylpalmitate, polyethylene glycol ethanol 95%, polyoxyethylene raonolauriate 5% in water, sodium lauryl sulfate 5% in water, and the like. In addition, materials such as antioxidants, humectants, viscosity stabilizers and the like also may be added.

For oral administration, the crystalline compound may be administered as a capsule, tablet or granule. Tablets may contain various excipients such as microcrystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinylpyrrolidone, sucrose, gelatin and acacia. In a certain embodiment, the tablet may be film coated. Additionally, lubricating agents such as magnesium stearate, sodium lauryl sulfate and talc are often very useful for tablets. Other solid compositions may also be employed as fillers in gelatin capsules; preferred materials in this connection also Include lactose or milk sugar as well as high molecular weight polyethylene glycols. When aqueous suspensions and/or elixirs are desired for oral administration, the crystalline compound may be combined with various sweetening or flavoring agents, coloring matter or dyes, and, if so desired, emulsifying and/or suspending agents, together with such diluents as water, ethanol, propylene glycol, glycerin and various like combinations thereof The pharmaceutical composition may be formulated such that the crystalline compound is released over a period of time after administration.

The pharmaceutical composition comprising the crystalline compound along with a pharmaceutically acceptable excipient and, optionally, an additional active ingredient, may be prepared by any conventional technique known in the art.

In an embodiment, the amount of crystalline compound present in the pharmaceutical composition is about 0.01% to about 90% by weight relative to the whole composition. A suitable therapeutically effective amount of the crystalline compound will typically range from about 0.01 mg/kg to about 1 g/kg of body weight per day; in another embodiment, from about 1 mg/kg to about 600 mg/kg body weight per day; in another embodiment, from about 1 mg/kg to about 250 mg/kg body weight per day; in another embodiment, from about 10 mg/kg to about 400 mg/kg body weight per day; in another embodiment, from about 10 mg/kg to about 200 mg/kg of body weight per day; in another embodiment, from about 10 mg/kg to about 100 mg/kg of body weight per day; in one embodiment, from about 10 mg/kg to about 25 mg/kg body weight per day; in another embodiment, from about 1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day. In a certain embodiment, when a pharmaceutical composition described herein is administered orally, a suitable therapeutically effective amount of the crystalline compound is about 0.01 to about 100 milligrams per kilogram of body weight of recipient per day, preferably about 0.1 to about 50 milligrams per kilogram body weight of recipient per day, and more preferably from about 0.1 to about 20 milligrams per kilogram body weight of recipient per day. The desired dose may be administered once daily, or by several sub-divided doses, e.g., 2 to 5 sub-divided doses, at appropriate intervals through the day, or other appropriate schedule.

The term "pharmaceutically acceptable excipient" as used herein includes, but is not limited to, one of more of the following: polymers, resins, plasticizers, fillers, lubricants, diluents, binders, disintegrants, solvents, co-solvents, surfactants, buffer systems, preservatives, sweetener agents, flavoring agents, pharamaceutical-grade dyes or pigments, chelating agents, viscosity agents, and combinations thereof. Pharmaceutically acceptable excipients can be used in any component in making the dosage form, i.e. core tablet or coating. Flavoring agents and dyes and pigments among those useful herein include but are not limited to those described in Handbook of Pharmaceutical Excipients (4th Ed., Pharmaceutical Press 2003). Suitable co-solvents include, but are not limited to, ethanol, isopropanol, acetone, and combinations thereof. Suitable surfactants include, but are not limited to, polyoxyethylene sorbitan fatty acid esters, polyoxyethylene monoalkyl ethers, sucrose monoesters, simethicone emulsion, sodium lauryl sulfate, Tween 80®, and lanolin esters, ethers, and combinations thereof. Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, propyl paraben, and combinations thereof. Suitable fillers include, but are not limited to, starch, lactose, sucrose, maltodextrin, and microcrystalline cellulose. Suitable plasticizers include, but are not limited to, tiethyl curate, polyethylene glycol, propylene glycol, dibutyl phthalate, castor oil acetylated monoglycerides, triacetin, and combinations thereof. Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, Eudragst® F530D and Eudragit® S 100 (Rohm Pharma GmbH and Co. KG, Darmstadt, Germany), Acryl-EZE® and Sureterie® (Coloreon, Inc. West Point, Pa.), and combinations Thereof. Suitable lubricants include, but are not limited to, magnesium stearate, stearic acid, talc, and combinations thereof.

The term "additional active ingredient" as used herein includes any agent known in the art to treat, prevent or reduce the symptoms of the condition being treated by the pharmaceutical composition. Such an agent, includes but is not limited to an agent known to treat, prevent or reduce uterine contractions or preterm labor, such as a calcium channel blocker, magnesium sulfate, a selective prostaglandin modulator, a beta-2-adrenergic agonist, a beta-3-adrenergic receptor agonist, a corticosteroid, and a mixture thereof.

Alternatively, the crystalline compound can be administered concomitantly or separately with at least one compound selected from the group consisting of a calcium channel blocker (such as nifedipine), magnesium sulfate, a prostaglandin receptors modulator (such as an agonist or antagonist of either EP1 or EP2 or EP3 or EP4 or FP receptor), a prostaglandin synthesis inhibitor (such as indomethacin, nimesulide, submiae, rofecoxib, celceoxib), a beta-2-adrenergic agonist (such as ritodrine, terbutaline, salbutamol), a beta-3-adrenergic receptor agonist, a nitric acid donor (such as glyceryl trinitrate), a corticosteroid (such as dexamethasone, betamethasone), and a mixture thereof. As used herein, "concomitantly" refers to administration of the crystalline compound immediately preceded or followed by administration of at least one compound. As used herein, "separately" encompasses sequential or subsequent administration and refers to the administration of the crystalline compound, followed by a time period of discontinuance, which is then followed by the administration of at least one compound.

The pharmaceutical composition may be used for treating a condition related to the OT-R activity, A certain embodiment is directed to a pharmaceutical composition comprising crystalline (3Z,5S)-5-(hydroxymethyl)-1-[(2'-methyl-1,1-biphenyl-4-yl)carbonyl]pyrrolidin-3-one O-methyloxime, and a pharmaceutically acceptable excipient for use in treating preterm labor, Methods of Use One embodiment of the invention is directed to a method for treating a condition related to the OT-R activity comprising administering to a subject a therapeutically effective amount of crystalline (3Z,5S)-5-(hydroxymethyl)-1-[(2'-methyl-1,1-biphenyl-4-yl)carbonyl]pyrrolidin-3-one O-methyloxime. In one embodiment, the invention is directed to a method of treating preterm labor.

The term "treating" as used herein includes therapeutic and/or prophylactic treatment of a condition related to the OT-R activity. The treatment includes the diminishment or alleviation of at least one symptom associated with the condition related to the OT-R activity or at least one symptom associated with another condition described herein.

The term "therapeutically effective amount" as used herein means an amount of a compound or composition high enough to significantly positively modify the symptoms and/or condition to be treated, but low enough to avoid serious side effects (at a reasonable risk/benefit ratio), within the scope of sound medical judgment. The therapeutically effective amount of the crystalline compound is selected in accordance with a variety of factors including type, species, age, weight, sex and medical condition of the patient; the severity of the condition to be treated; the route of administration; the renal and hepatic function of the patient. A physician of ordinary skill in the art can readily determine and prescribe the effective amount of the drug required to prevent, counter or arrest the progress of the condition.

The term "subject" as used herein is an animal. "Subject" includes, without limitation, a human, mouse, rat, guinea pig, dog, cat, horse, cow, pig, monkey, chimpanzee, baboon, or rhesus monkey. In one embodiment, "subject" is a mammal. In another embodiment, "subject" is a human, preferably a human female, and more preferably, a human female of child bearing age.

In an embodiment, the therapeutically effective amount of the crystalline compound is administered in a single dose, and that single dose is between about 10 mg and about 1000 mg, preferably between about 50 mg and about 900 mg, and more preferably between about 100 mg and about 600 mg. The crystalline compound may be administered at least once weekly, bi-weekly, daily, or multiple limes per day. It may be administered in a single dose, or the total dosage may be administered in divided doses of two, three or four times dally.

In an embodiment, crystalline (3Z,5S)-5-(hydroxymethyl)-1-[(2'-methyl-1,1-biphenyl-4-yl)carbonyl]pyrrolidin-3-one O-methyloxime is administered orally, topically, vaginally, rectally, or parenterals, preferably, it may be administered intravenously or orally, and more preferably, it may be administered orally.

With respect to treating preterm labor, the crystalline compound may rapidly decrease the frequency of and halt uterine contractions in about 2 to about 30 minutes following its administration, and preferably about 5 to about 20minutes following its administration.

Another embodiment of the invention is directed to a method for increasing embryo implantation rate in a female mammal undergoing embryo transfer comprising administering to a subject a therapeutically effective amount of crystalline (3Z,5S)-5-(hydroxymethyl)-1-[(2'-methyl-1,1-biphenyl-4-yl)carbonyl]pyrrolidin-3-one O-methyloxime. In a preferred embodiment thereof the mammal is a human, and, more preferably, a human female of child bearing age.

The "embryo implantation rate" relates to the number of embryos that adhere to the endometrium of the mammal after fertilization generated using Assisted Reproductive Technology (ART). A high embryo implantation rate refers to a high potential that the embryo when transferred into the uterus will be implanted in the uterine environment and give rise to a viable fetus.

Embryo transfer is understood to be in connection with ART. It is a reproduction technique wherein embryos are generated in a laboratory by fertilization using eggs of a receptor female or a separate donor female and then transferred to the uterus of a receptor female mammal.

The definitions and preferred embodiments disclosed above with respect the other embodiments are the same for this embodiment.

A further embodiment of the invention is directed to a method for preparing a crystalline compound of (3Z,5S)-5-(hydroxymethyl)-1-[(2'-methyl-1,1-biphenyl-4-yl)carbonyl]pyrrolidin-3-one O-methyloxime, which comprises i) dissolving a substantially pure Z form of (3Z,5S)-5-(hydroxymethyl)-1-[(2'-methyl-1,1-biphenyl-4-yl)carbonyl] pyrrolidin-3-one O-methyloxime with a solvent selected from the group consisting of ethyl acetate and diethyl ether ii) allowing the crystals to form, iii) removing the solvent and concentrating the solution to dryness to provide the formed crystals.

When the substantially pure Z form of (3Z,5S)-5-(hydroxymethyl)-1-[(2'-methyl-1,1-biphenyl-4-yl)carbonyl] pyrrolidin-3-one O-methyloxime is contacted with ethyl acetate, said suspension is then sonicated in ambient bath for about 60 minutes to provide a clear solution which is further sonicated and cooled over about 10 minutes, ii) the crystals are allowed to form for about 4 days at a temperature between −15° C. to −25° C., iii) the solvent ethyl acetate is then removed by decantation, the solid washed with hexane and dried under nitrogen flow for about 30 minutes.

When the substantially pure Z form of (3Z,5S)-5-(hydroxymethyl)-1-[(2'-methyl-1,1-biphenyl-4-yl)carbonyl] pyrrolidin-3-one O-methyloxime is contacted with diethyl ether, the solid y then dissolved by swirling and the clear solution is left to stand at 18-23° C., ii) the crystals are allowed to form about 20 hours at about 18-23° C. and iii) crystals are isolated by filtration and dried under nitrogen to remove the solvent diethyl ether for about 4 hours at about 18-23° C.

The following examples will illustrate the practice of the present invention in some of the preferred embodiments. Other embodiments within the scope of the claims will be apparent to one skilled in the art.

EXAMPLES

The following examples illustrate the synthesis of the compounds described herein.

Synthesis and purification of (3Z,5S)-5-(hydroxymethyl)-1-[(2'-methyl-1,1-biphenyl-4-yl)carbonyl] pyrrolidin-3-one O-methyloxime (amorphous form)

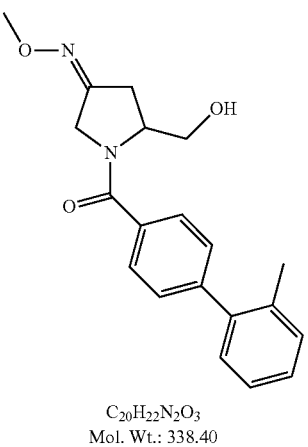 [SMILES: CO/N=C1/CC(CO)N(C(=O)c2ccc(-c3ccccc3C)cc2)C1]

C$_{20}$H$_{22}$N$_2$O$_3$
Mol. Wt.: 338.40

Synthesis and purification of (3Z,5S)-5-(hydroxymethyl)-1-[(2'-methyl-1,1-biphenyl-4-yl)carbonyl]pyrrolidin-3-one O-methyloxime is set forth in European Application No. 13183723.9, the contents of which are incorporated herein by reference in its entirety.

1.1 Synthesis of (3Z/E,5S)-5-(hydroxymethyl)-1-[(2'-methyl-1,1-biphenyl-4-yl)carbonyl]pyrrolidin-3-one O-methyloxime (3Z,5S)-5-(hydroxymethyl)-1-[(2'-methyl-1,1-biphenyl-4-yl)carbonyl]pyrrolidin-3-one O-methyloxime is obtained as a crude isomeric mixture comprising (3Z,5S)-5-(hydroxymethyl)-1-[(2'-methyl-1,1-biphenyl-4-yl)carbonyl] pyrrolidin-3-one O-methyloxime and (3E,5S)-5-(hydroxymethyl)-1-[(2'-methyl-1,1-biphenyl-4-yl)carbonyl] pyrrolidin-3-one O-methyloxime. Synthetic pathways of compounds of the invention are for example those described in WO 2004/005249 and WO 2005/082848.

"(3Z,5S)-5-(hydroxymethyl)-1-[(2'-methyl-1,1-biphenyl-4-yl)carbonyl]pyrrolidin-3-one O-methyloxime" is also defined as "(4Z,2S)-2-(hydroxymethyl)-1-[(2'-methyl-1,1-biphenyl-4-yl)carbonyl]pyrrolidin-4-one O-methyloxime-" depending on the nomenclature used.

For example, compound of the invention (3Z/E,5S)-5-(hydroxymethyl)-1-[(2'-methyl-1,1-biphenyl-4-yl)carbonyl] pyrrolidin-3-one O-methyloxime can also be prepared following stages 1 to 7 as described below:

Stage 1: Preparation of 4-(2-methylphenyl)benzoic acid

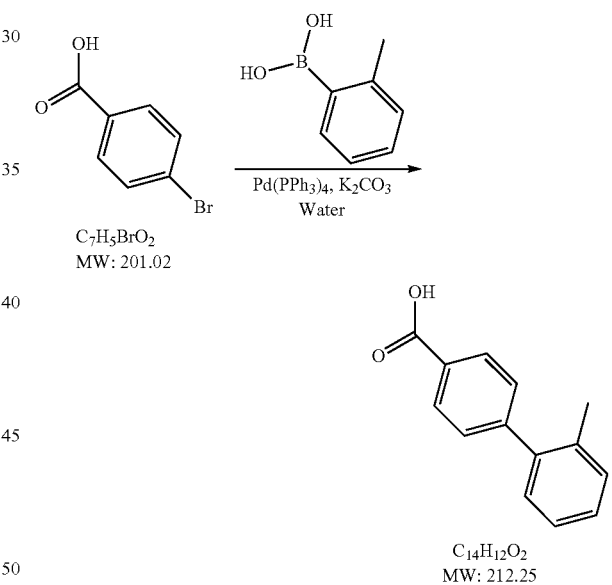

A solution of potassium carbonate (0.908 Kg, 6.57 mol, 2.06 wt) in water (2.20 L, 5.0 vol) was charged to a slurry of 4-bromobenzoic acid (0.441 Kg, 2.19 mol, 1.0 wt) in water (4.41 L, 15.0 vol) at 15 to 25° C. The resulting slurry was stirred at 15 to 25° C. and degassed three times using a vacuum-nitrogen purge cycle. Tetrakis(triphenylphosphine)palladium(0) (0.22 Kg, 0.019 mol, 0.05 wt) was charged and the vacuum-nitrogen purge cycle repeated. A solution of o-tolyboronic acid (0.313 Kg, 2.30 mol, 0.707 wt) in methanol (3.53 L, 8.0 vol) was degassed three times, using a vacuum-nitrogen purge cycle, and then charged to the 4-bromobenzoic acid slurry at 15 and 25° C. The reaction mixture was heated to and maintained at reflux (71 to 78° C.) until reaction completion (The reaction is considered complete at 95% conversion), as determined by $^1$H NMR analysis (d6-

DMSO), typically 1.5 to 2.5 hours. The reaction mixture was concentrated to 15 vol under vacuum at 40 to 45° C. Toluene (4.41 Km 10.0 vol) and tetrahydrofuran (4.41 L, 10.0 vol) were added to the residue, the resulting mixture stirred vigorously and acidified to pH 1 with hydrochloric acid (6M, 2.00 L, 4.5 vol). The contents were stirred vigorously tor 30 to 60 minutes and the layers separated. Toluene (2.20 L, 5.0 vol) and tetrahydrofuran (2.20 L, 5.0 vol) were added to the aqueous phase and the mixture stirred for 5 to 10 minutes. The layers were separated, the combined organic phases filtered and concentrated to 10.0 vol under vacuum at 35 to 40° C. Toluene (4.41 L, 10.0 vol) was added to the residue and the resultant concentrated under vacuum at 35 to 40° C. The tetrahydrofuran content of the resulting slurry was determined by 'H NMR analysis (d6-DMSO) (Pass level: ≤1.0% w/w tetrahydrofuran with respect to toluene). The slurry was cooled to and aged at 0 to 5° C. for 30 to 60 minutes, the solid collected by filtration and the filter-cake washed with toluene (2.20 L, 5.0 val). The solid was dried in a vacuum oven at 35 to 40° C. to give 4-(2-methylphenyl) benzoic acid [0.438 Kg, 94.1% th, 99.3% w/w, III NMR. (d6-DMSO) concordant with structure] as a pale yellow solid.

Stage 2: Preparation of 4-(2-methylphenyl)benzoic acid chloride

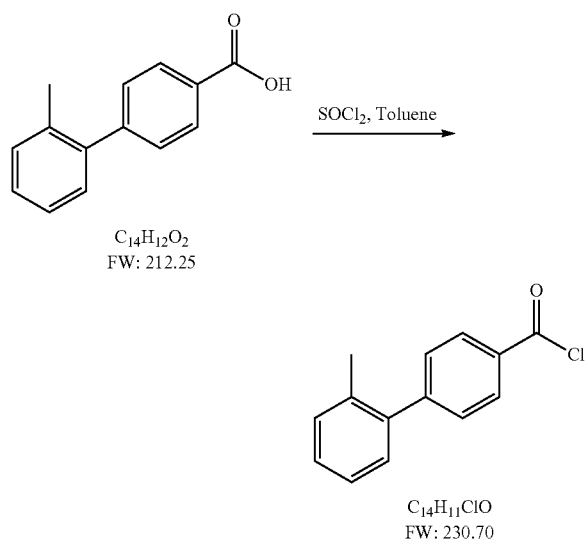

Thionyl chloride (0.300 L, 4.11 mol, 0.685 vol) was added to a slurry of 4-(2-methylphenyl)benzoic acid (0.435 Kg, 2.05 mol, 1.0 wt) in toluene (4.35 L, 10.0 vol) at 10 to 25° C. and the mixture heated to and maintained at 75 to 80° C. until complete by 1H NMR analysis (d6-benzene), typically 4 to 5 hours. Reaction completion was accompanied by the formation of a hazy solution. The resultant was concentrated to 5.0 vol by removal of toluene under reduced pressure at 35 to 45° C. Toluene (2.18 L, 5.0 vol) was added to the concentrate and the mixture concentrated to 4.0 vol by removal of toluene under reduced pressure at 35 to 45° C. The resultant was filtered through glass microfibre paper and the filter-cake washed with toluene (0.44 L, 1.0 vol). The toluene solution of 4-(2-methylphenyl)benzoic acid chloride [0.439 Kg, 92.8% th, 100.9% w/w, 1H NMR (d6-benzene) concordant with structure] was used directly in Stage 3.

Stage 3: Preparation of (4R)-4-hydroxy-1-[(2'-methyl-1,1'-biphenyl-4yl)-carbonyl]-L-proline

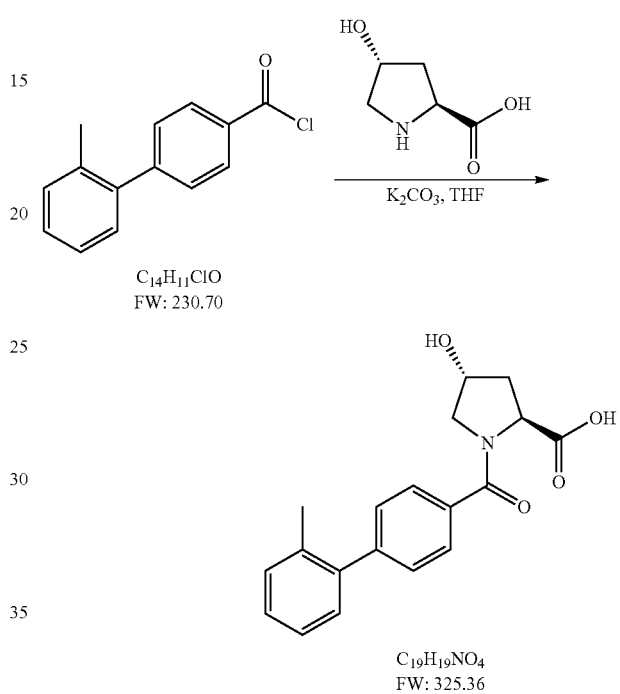

A solution of potassium carbonate (0.526 Kg, 3.81 mol, 1.2 wt) in water (0.57 L, 1.3 vol) was charged to a solution of 4-hydroxy-L-proline (0.274 Kg, 2.09 mol, 0.625 wt) in tetrahydrofuran (2.20 L, 5.0 vol) and water (0.44 L, 1.0 vol) at 15 to 25° C. followed by a line rinse of wafer (0.44 L, 1.0 vol). The mixture was cooled to 0 to 5° C. with rapid stirring and a solution of 4-(2-methylphenyl)benzoic acid chloride (0.438 Kg, 1.90 mol, 1.0 wt) in toluene (2.19 L, 5.0 vol) charged at that temperature followed by a line rinse of toluene (0.44 L, 1.0 vol). The reaction mixture was warmed to 15 to 25° C. over 1 to 2 hours and stirred at this temperature until judged complete by TLC analysis. Water (2.20 L, 5.0 vol) was charged to the reaction mixture at 15 to 25° C. and the layers separated. The aqueous phase was acidified to pH 5 to 6 with aq. hydrochloric acid (6M, 0.66 L, 1.5 vol) and then to pH1 with aq. hydrochloric acid (2M, 0.88 L, 2.0 vol) at 15 to 25° C. The mixture was cooled to and aged at 0to 5° C. for 30 to 60 minutes, the precipitated solid collected by filtration, the filter-cake washed with water (2×1.75 L, 2×4.0 vol) and toluene (0.88 L, 2.0 vol) and pulled dry on the filter for 12 to 24 hours. The collected solid was dried under vacuum at 40 to 45° C. until the water content by KP was ≤0.2% w/w to afford (4R)-4-hydroxy-1-[(2'-methyl-1,1'-biphenyl-4-yl)carbonyl]-L-proline [0.599 Kg, 97.0% th, 136.8% w/w, $^1$H NMR (d$_6$-DMSO) concordant with structure] as an off-white solid.

Stage 4: Preparation of 1-(2'-methyl-1,1-biphenyl-4-yl)carbonyl-4-oxo-L-proline

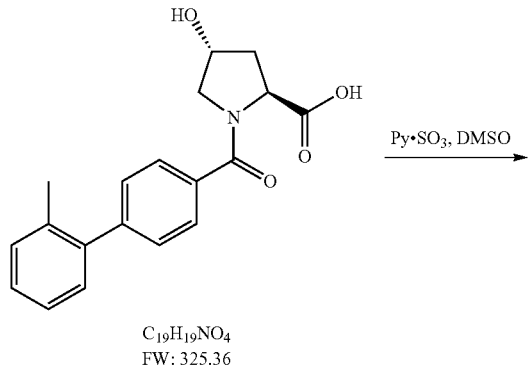

C$_{19}$H$_{19}$NO$_4$
FW: 325.36

Py·SO$_3$, DMSO

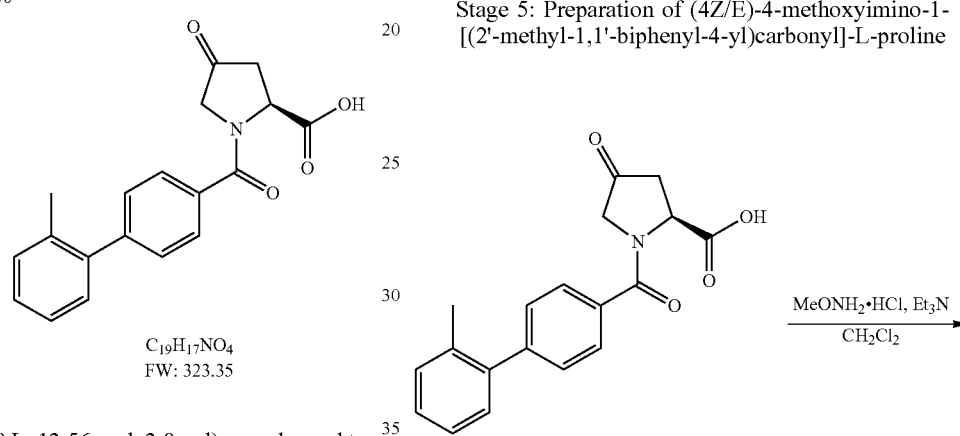

C$_{19}$H$_{17}$NO$_4$
FW: 323.35

Triethylamine (1.80 L, 13.56 mol, 3.0 vol) was charged to a solution of (4R)-4-hydroxy-1-[(2'-methyl-1,1'-biphenyl-4-yl)carbonyl]-L-proline (0.598 Kg, 1.84 mol, 1.0 wt) in dimethyl sulfoxide (4.42 L, 7.4 vol) at 15 to 20° C. Pyridine-sulphur trioxide complex (0.879 Kg, 5.52 mol, 1.47 wt) was charged portion-wise at 15 and 25° C. and the reaction mixture stirred at that temperature until reaction completion, as determined by TLC analysis (typically 1 to 3 hours). 7 The reaction was quenched with aq. hydrochloric acid (3M, 4.80 L, 8.0 vol) at 0 to 30° C. tetrahydrofuran (3.00 L, 5.0 vol) and heptanes (0.60 L, 1.0 vol) charged, the layers separated and the aqueous phase extracted with tetrahydrofuran (2×300 L, 2×5.0 vol). The combined organic phases were washed with aq. hydrochloric acid (1 M, 2×1.20 L, 2×2.0 vol) and saturated sodium chloride solution (2×1 20 L, 2×2.0 vol), the aqueous washes combined and back-extracted with tetrahydrofuran (2×0.60 L, 2×1.0 vol). The combined organics were dried over magnesium sulphate (1.794 Kg, 3.0 wt), filtered, the filtercake washed with tetrahydrofuran (0.60 L, 1.0 vol) and the filtrates concentrated under vacuum at 40 to 45° C. to give a pale brown foam. Ethyl acetate (6.00 L, 10.0 vol) was charged to the foam, the contents stirred for 5 to 10 minutes to reach dissolution and the solvent removed under vacuum at 40 to 45° C. This was repeated using ethyl acetate (6.00 L, 5.0 vol) until tetrahydrofuran was not detected by $^1$H NMR analysis (d6-DMSO). The residue was slurried in ethyl acetate (4.80 L, 8.0 vol), activated carbon (0.084 Kg, 0.14 wt) added followed by a line rinse of ethyl acetate (3.00 L, 5.0 vol), the resultant heated to and maintained at 70 to 80° C. for 20 to 30 minutes, cooled to 40 to 55° C. and filtered through glass microfibre paper, The filter-cake was washed with ethyl acetate (1.50 L, 2.5 vol) and the combined filtrates and wash concentrated to 2.5 to 3.5 vol under vacuum at 40 to 45° C. Crystallization commenced during the concentration. The concentrate was transferred to a suitable vessel with a line rinse of ethyl acetate (0.30 L, 0.5 vol) and heated to 70 to 80° C. Additional ethyl acetate (0.30 L, 0.5 vol) was added as necessary to achieve dissolution. Heptanes (1.80L, 3.0 vol) was added at 70 to 80° C. and the contents allowed to cool to between 15 and 25° C. over 1 to 2hours. The slurry was further cooled to and aged at 0 to 5° C. for 2 to 3 hours, filtered and the filtercake washed with ethyl acetate:heptanes (1:1, 0.60 L, 1.0 vol) at 0 to 5° C. followed by heptanes (3.0 L, 2.5 vol). The collected solid was dried under vacuum at 40 to 45° C. to give 1-[(2'-methyl-1,1'-biphenyl-4-yl)carbonyl]-4-oxo-L-proline [0.444 Kg, 74.7% th, 74.2% w/w, $^1$H NMR (d6-DMSO) concordant with structure] as an off-white solid.

Stage 5: Preparation of (4Z/E)-4-methoxyimino-1-[(2'-methyl-1,1'-biphenyl-4-yl)carbonyl]-L-proline

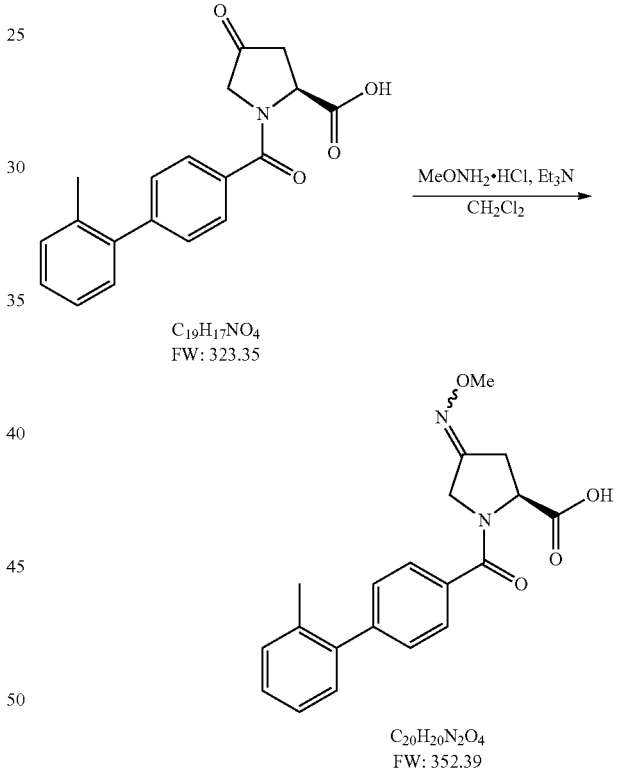

C$_{19}$H$_{17}$NO$_4$
FW: 323.35

MeONH$_2$·HCl, Et$_3$N
CH$_2$Cl$_2$

C$_{20}$H$_{20}$N$_2$O$_4$
FW: 352.39

Triethylamine (0.40 L, 2.85 mol, 0.92 vol) was added to a solution of 1-[(2'-methyl-1,1'-biphenyl-4-yl)carbonyl]-4-oxo-L-proline (0.434 Kg, 1.34 mol, 1.0 wt) in dichloromethane (4.40 L, 10.0 vol) at 10 to 25° C. followed by a line rinse of dichloromethane (0.43 L, 1.0 vol). Methoxylamine hydrochloride (0.130 Kg, 1.56 mol, 0.30 wt) was added portion-wise at 10 to 25° C. followed by a line rinse of dichloromethane (0.43 L, 1.0 vol) and the reaction mixture stirred at 10 to 25° C. until reaction completion, as determined by TLC analysis (typically 3 to 5 hours, TLC eluent: dichloromethane:methanol:acetic acid (90:10:1); uv visualization). The solvent was removed under vacuum at 35 to 40° C., the resultant dissolved in ethyl acetate (4.40 L, 10.0 vol) and washed with aq. hydrochloric acid (1 M, 2×2.20 L, 2×5.0 vol). The acidic washes were back extracted with ethyl acetate (2.20 L, 5.0 vol), the combined organic phases washed with sat, aq, sodium chloride solution (3.10 L, 7.0 vol), dried over magnesium sulfate (0.300 Kg, 0.69 wt). filtered and the filtercake washed with ethyl acetate (2.20 L, 5.0 vol). The filtrate and washes were combined and concentrated under vacuum at 35 to 40° C. to afford 4- methoxyimino-1-[(2'-methyl-1,1'-biphenyl-4-yl)carbonyl]-L-proline [0.476 Kg, 100.6% th, 109.6% w/w, $^1$H NMR (CDCl$_3$) concordant with structure) as an off-white solid.

Stage 6: Preparation of (4Z/E, 2S)-methyl-1-[(2'-methyl-1,1'-biphenyl-4-yl)-carbonyl]-4-methoxy-imine Pyrrolidine-2-carboxylate

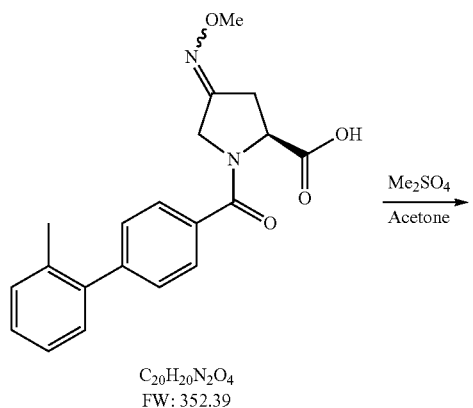

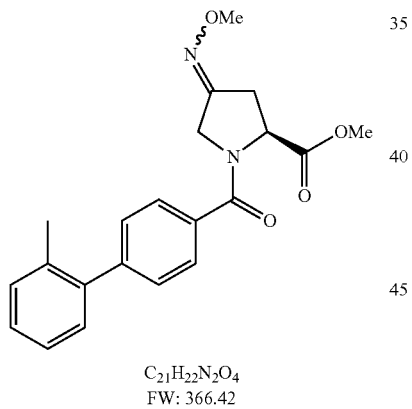

Potassium carbonate (0.476 Kg, 3.44 mol, 1.0 wt) was added to a solution of 4-methoxyimino-1-[(2'-methyl-1,1-biphenyl-4-yl)carbonyl]-L-proline (0.475 Kg, 1.35 mol, 1.0 wt) in acetone (4.75 L, 10.0 vol) and the mixture cooled to 0 to 10° C. Dimethyl sulfate (0.128 L, 1.35 mol, 0.27 vol) was added at 0 to 15° C. and the mixture stirred at 15 to 25° C. until reaction completion, as determined by TLC analysis, typically 3 to 16 hours. The solvent was removed under vacuum at 40 to 45° C. and the resultant partitioned between ethyl acetate (3.80 L, 8.0 vol) and water (3.80 L, 8.0 vol). The layers were separated, the organic phase washed with sat. aq. sodium chloride solution (2.85 L, 6.0 vol), dried over sodium sulfate (0.953 Kg, 2.0 wt) and filtered. The filter-cake was washed with ethyl acetate (0.48 L, 1.0 vol) arid the combined filtrate and wash concentrated under vacuum at 40 to 45° C. Excess ethyl acetate was removed by axeotropic distillation with tetrahydrofuran (2×0.95 L, 2×2.0 vol) under vacuum at 40 to 45° C. to give (4Z/E, 2S)-methyl-1-[(2'-methyl-1,1'-biphenyl-4-yl)-carbonyl]-4-methoxyimino pyrrolidine-2-carboxylate [0.492 Kg, 99.6% th, 103.6% w/w, $^1$H NMR (CDCl$_3$) concordant with structure] as a viscous brown oil.

Stage 7: Preparation of (3Z/E,5S)-5-(hydroxymethyl)-1-[(2'-methyl-1,1'-biphenyl-4-yl)carbonyl] pyrrolidin-3-one O-methyloxime

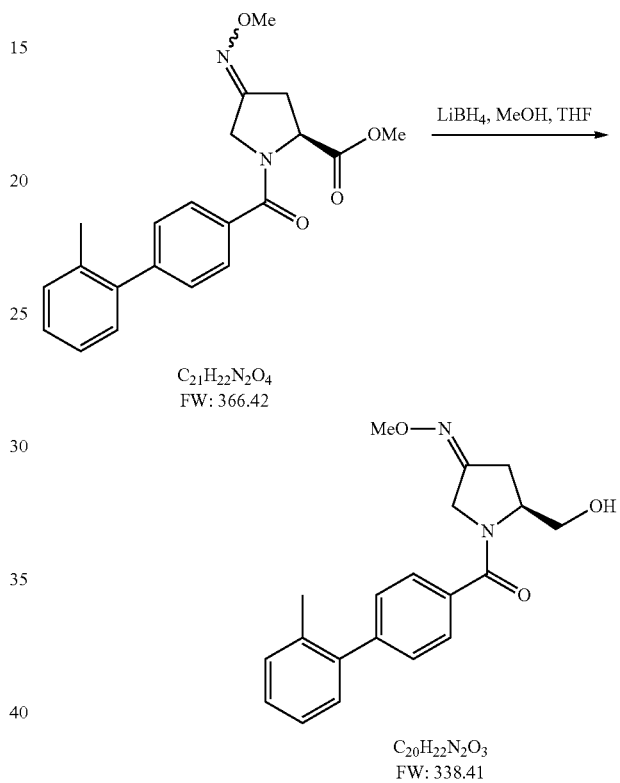

Lithium borohydride (0.049 Kg. 2.26 mol, 0.1 wt) was added portionwise under nitrogen to a stirred solution of 4Z/E, 2S)-methyl-1-[(2'-methyl-1,1'-biphenyl-4-yl)-carbonyl]-4-methoxyimino pyrrolidine-2-carboxylate 0.492 kg. 1.34 mol, 1.0 wt) in tetrahydrofuran (2.31 L, 4.7 vol) and methanol (2.31 L, 4.7 vol) at 0 to 30° C. The mixture was stirred at 15 to 25° C. to reaction completion, as determined by TLC analysis (Eluent; ethyl acetate; Visualisation: ninhydrin), typically 2 to 6 hours. The reaction mixture was quenched with water (0.40 L, 0.8 val) at 15 to 25° C. and stirred at 15 to 25° C. for 16 to 20 hours. The resultant was concentrated under vacuum at 40 to 45° C. and the residue partitioned between water (2.46 L, 5.0 vol) and ethyl acetate (4.92 L, 10.0 vol). The layers were separated, the organic phase washed sequentially with aq. hydrochloric acid (1M, 2.46 L, 5.0 vol), sat. aq. sodium hydrogen carbonate solution (2.46 L, 5.0 vol) and sat. aq. sodium chloride solution (2.46 L, 5.0 vol). The organic phase was dried over magnesium sulfate (0.985 Kg, 2.0 wt), filtered and the filter-cake washed with ethyl acetate (0.50 L, 1.0 vol). The combined filtrate and wash were concentrated under vacuum to give a crude isomeric mixture comprising (3Z,5S)-5-(hydroxymethyl)-1-[(2'-methyl-1,1'-biphenyl-4-yl)carbonyl]pyrrolidin-3-one O-methyloxime and (3E,5S)-5-(hydroxymethyl)-1-[(2'-methyl-1,1'-biphenyl-4-yl)carbonyl]pyrrolidin-3-one O-methyloxime [0.395 Kg, 86.9% th, 80.3% w/w, 1H NMR (CDCl$_3$) concordant with structure; 82.0% area by HPLC, 71.4:28.6 Z/E Ratio]as a viscous brown oil. The oil was dissolved in toluene (0.40 L, 1.0 vol, with respect to weight of product) and stored until required.

1.2 Substantially Pure Form of (3Z,5S)-5-(hydroxymethyl)-1-[(2'-methyl-1,1'-biphenyl-4-yl)carbonyl]pyrrolidin-3-one O-methyloxime

1.2.1 Small Scale Purification

The isolation procedure in substantially pure form (3Z,5S)-5-(hydroxymethyl)-1-[(2'-methyl-1,1'-biphenyl-4-yl)carbonyl]pyrrolidin-3-one O-methyloxime was performed by chromatography using a Biotage system (Biotage AB, SE-751 03 Uppsala, Sweden) of the crude isomeric mixture isolated after reduction of the oxime ester (Stage 7 of Example 1).

Five distinct batches (No. 020, 180, 062, 068, 076) of the crude isomeric mixture were purified by Biotage chromatography. Furthermore, different conditions were used regarding batches No. 068 and 076. Purification was performed with a 5% w/w spike of oxime methyl ester added (No. 068). and with an overloaded Biotage column (No. 076).

Each chromatography was run using Biotage 40M cartridges (40 g silica) which had been pre-flushed with toluene. Toluene:MeOH (99:1 v/v) was then eluted and collected in 100 ml fractions (total volume 4 L), followed by a flush of toluene:MeOH (96:4 v/v).

Fractions were analysed by TLC (eluent; ethylacetate) to determine which fractions could be discarded and which fractions contained Z isomer. These Z fractions were then analyzed by HPLC. The pass criteria, for a fraction was >96% Z isomer and <1.2% E isomer.

Surprisingly, the purification through Biotage chromatography of various batches was very efficient as the substantially pure form of (3Z,5S)-5-(hydroxymethyl)-1-[(2'-methyl-1,1'-biphenyl-4-yl)carbonyl]pyrrolidin-3-one O-methyloxime is purified at 99.4% (Batches No. 020, No. 062, No. 068) and at 99.2% (Batches No. 180, No. 076). In particular, the Biotage chromatography in presence of oxime ester removes 5% w/w ovime ester without detriment to recovery or quality (Batch No. 068) and a 25% overcharge of the Biotage column does not cause a decrease in yield or quality(batch No. 076).

TABLE 2

Efficiency of the Biotage chromatography

| Batch No. | Input % E/Z | Output % E/Z | yield of Z isomer |
|---|---|---|---|
| 020 | 3.0 g<br>85.7% area purity<br>% E/Z: 30.5/69.5 | Pure Z-fractions:<br>1.0 g<br>98.8% area purity<br>% E/Z: 0.6/99.4 | 33% |
| 180 | 2.0 g<br>92.0% area purity<br>% E/Z: 32.8/67.2 | Pure Z-fractions<br>0.9 g<br>99.6% area purity<br>% E/Z: 0.8/99.2 | 45% |
| 062 | 3.0 g<br>83.5% area purity<br>% E/Z: 32.7/67.3 | Pure Z-fractions<br>1.3 g<br>99.8% area purity<br>% E/Z: 0.6/99.4<br>Mixture:<br>1.2 g<br>91.0% area purity<br>% E/Z: 69.6/30.4 | 43%<br><br><br><br>11% |
| 068 | 3.0 g spiked with ~5% ester<br>~78% area purity<br>% E/Z: 32.7/67.3 | Pure Z fractions:<br>1.2 g<br>99.8% area purity<br>% E/Z: 0.6/99.4<br>Mixture:<br>0.6 g<br>98.8% area purity<br>% E/Z: 27.9/72.1<br>Pure E fractions:<br>1.1 g<br>70.7% area purity<br>% E/Z: 98.7/1.3<br>(19.3% ester) | 40%<br><br><br><br>14%<br><br><br><br>N/A |
| 076 | 3.8 g<br>83.5% area purity<br>% E/Z: 32.7/67.3 | Pure Z fractions<br>1.4 g<br>99.8% area purity<br>% E/Z: 0.8/99.2<br>Mixture:<br>1.8 g<br>95.0% area purity<br>% E/Z: 63.6/36.4 | 37%<br><br><br><br>17% |

1.2.2 Large Scale Purification

Various batches of crude (3Z,5S)-5-(hydroxymethyl)-1-[(2'-methyl-1,1'-biphenyl-4-yl)carbonyl]pyrrolidin-3-one O-methyloxime (0.392 kg, 1.16 mol, 1.0 wt) were charged to a Biotage 150 L SIM unit as an approximate 50% w/w solution in toluene and purified using 1% methanol in toluene (150 L) followed by 2% methanol in toluene (50 L), fraction size 5.0 L. The collected fractions were analysed by TLC[15] and HPLC analyses, as appropriate. The fractions that were deemed to contain clean (3Z,5S)-5-(hydroxymethyl)-1-[(2'-methyl-1,1'-biphenyl-4-yl)carbonyl]pyrrolidin-3-one O-methyloxime (criteria: Z-isomer ≥96.00% area, E-isomer≤1.20% area) were combined and concentrated under vacuum at 40 to 45° C. Absolute ethanol (2×2 L) was added to the residue and the solution concentrated under vacuum at 40 to 45° C. until the foamy solid could be manipulated. The desired product, (3Z,5S)-1-[(biphenyl-4-yl)-5-hydroxy-methyl]pyrrolidin-3-one-O-methyloxime (0.089 Kg, 22.7% w/w, $^1$H NMR (CDCl$_3$) concordant with structure, 99.3% area by HPLC, 98,4:0.9 Z/E ratio was obtained as an off-white to light brown solid.

TABLE 3

Summary of purification of different batches of (3Z,5S)-5-(hydroxymethyl)-1-[(2'-methyl-1,1'-biphenyl-4-yl)carbonyl]pyrrolidin-3-one O-methyloxime in substantially pure form.

| Batch No. | Input (kg) | Output (kg) | Yield (% w/w) | % Z form (% area) | % E form (% area) |
|---|---|---|---|---|---|
| 12 | 0.392 | 0.089 | 22.8 | 98.65 | 0.85 |
| 116 | 0.392 | 0.114 | 29 | 98.34 | 0.89 |
| 120 | 0.441 | 0.081 | 18.4 | 97.90 | 1.81 |
| 122 | 0.380 | 0.094 | 24.3 | 98.52 | 1.14 |
| 124 | 0.387 | 0.096 | 25.3 | 98.89 | 0.73 |
| 126 | 0.390 | 0.132 | 33.8 | 98.40 | 0.95 |
| 128 | 0.526 | 0.010 | 2 | 98.20 | 0.83 |
| 130 | 0.453 | 0.086 | 19 | 98.46 | 1.23 |
| 132 | 0.440 | 0.082 | 19.3 | 98.86 | 0.85 |
| 134 | 0.39 | 0.144 | 36.9 | 98.73 | 0.96 |
| 138 | 0.273 | 0.098 | 35.9 | 98.92 | 0.66 |
| 140 | 0.463 | 0.059 | 13.1 | 98.52 | 1.13 |
| 142 | 0.462 | 0.084 | 18.4 | 99.37 | 0.48 |

TABLE 3-continued

Summary of purification of different batches of (3Z,5S)-5-(hydroxymethyl)-1-[(2'-methyl-1,1'-biphenyl-4-yl)carbonyl]pyrrolidin-3-one O-methyloxime in substantially pure form.

| Batch No. | Input (kg) | Output (kg) | Yield (% w/w) | % Z form (% area) | % E form (% area) |
|---|---|---|---|---|---|
| 144 | 0.442 | 0.126 | 29 | 99.1 | 0.68 |
| 146 | 0.409 | 0.135 | 33.5 | 99.21 | 0.46 |
| 148 | 0.460 | 0.107 | 23.8 | 99.13 | 0.65 |
| 150 | 0.409 | 0.071 | 18 | 98.92 | 0.66 |
| 152 | 0.392 | 0.054 | 14.3 | 98.82 | 0.76 |
| 156 | 0.445 | 0.039 | 8.8 | 98.64 | 0.87 |
| 158 | 0.392 | 0.06 | 15.3 | 98.73 | 0.63 |
| 162 | 0.435 | 0.150 | 34.5 | 98.94 | 0.79 |
| 164 | 0.434 | 0.192 | 44.2 | 99.21 | 0.58 |
| 166 | 0.415 | 0.074 | 17.8 | 98.79 | 0.73 |
| 174 | 0.518 | 0.108 | 20.8 | 99.11 | 0.64 |
| 176 | 0.342 | 0.072 | 21 | 98.88 | 0.77 |
| 178 | 0.415 | 0.074 | 17.8 | 99.07 | 0.71 |
| 180 | 0.353 | 0.174 | 49.3 | 99.03 | 0.82 |
| 182 | 0.270 | 0.178 | 65.9 | 99.10 | 0.53 |

Appropriate batches of (3Z,5S)-5-(hydroxymethyl)-1-[(2'-methyl-1,1'-biphenyl-4-yl)carbonyl]pyrrolidin-3-one O-methyloxime (2.713 kg, 1.0 wt) isolated from the Biotage chromatography were combined and dissolved in absolute ethanol (5.16 L, 2.0 vol) at 15 to 25° C., clarified by filtration through glass microfibre paper and an absolute ethanol wash (0.50 L, 0.2 vol) applied to the filter. The combined filtrates were concentrated portion wise under vacuum at 40 to 45° C. The resultant was transferred to drying trays and dried under vacuum at 30° C. for 24 hours, The oven temperature was then increased incrementally from 30 to 40° C. over 80 hours. The level of residual solvent was determined by $^1$H NMR analysis (CDCl$_3$) and when found to be <1.0 % w/w the solid was passed through a 500 μm aperture sieve. The solid was returned to the oven and dried at 40° C. to 42° C. until the solvent level was ≤0.40% w/w to afford (3Z,5S)-1-[(biphenyl-4yl-carbonyl)-5-hydroxy-methyl]-pyrrolidine-3-one-O-methyloxime in the amorphous form (2.633 Kg, 97.1% w/w, 1H NMR (CDCl3) concordant with structure, 98.65% area by HPLC.

The combination procedure is summarized below:

Input: 2.713 kg

Output: 2.633 kg

Yield: 97.1% w/w

Synthesis of Crystalline (3Z,5S)-5-(hydroxymethyl)-1-[(2'-methyl-1,1'-biphenyl-4-yl)carbonyl]pyrrolidin-3-one O-methyloxime (the "Crystalline Compound").

A series of experiments were conducted before successful crystallization was achieved. The foiled crystallization attempts included use of acetone, ACN, CH$_2$CL$_2$, 1,4-dioxane, ethanol, hexanes, IPA, methanol, MEK, TFE, THF, Toluene and water, among other solvents. After each of these experiments, the resulting solid was tested and XRPD analysis showed the compound to be in the amorphous form.

2.1 Crystallization using Ethyl Acetate

Ethyl acetate was added to amorphous (3Z,5S)-5-(hydroxymethyl)-1-[(2'-methyl-1,1'-biphenyl-4-yl)carbonyl]pyrrolidin-3-one O-methyloxime. The suspension was sonicated in ambient bath tor 60 minutes to provide a clear solution that was further sonicated and cooled over 10 minutes. The clear solution was placed in the freezer for 4 days. The solvent was decanted and the solid was washed with hexane, then dried under nitrogen flow for 30 minutes. The resulting solid was analyzed by XRPD and confirmed to be crystalline (3Z,5S)-5-(hydroxymethyl)-1-[(2'-methyl-1,1'-biphenyl-4-yl)carbonyl]pyrrolidin-3-one O-methyloxime. FIGS. 7 and 9 are the DSC and TGA curves, respectively, obtained front testing this sample. Characterization data is presented in Table 4.

TABLE 4

Characterization data of cyrstalline (3Z,5S)-5-(hydroxymethyl)-1-[2'-methyl-1,1'-bisphenyl-4-yl)carbonyl]pyrrolidin-3-one O-methyloxime from ethyl acetate

| Analytical Technique | Experiment Description | Result |
|---|---|---|
| XRPD | — | Crystalline form |
| DSC | 10° C./min, | Endo 72° C., baseline shift 127° C., Exo 232° C. |
| TGA | 25 to 350° C. | 3.2% weight loss at 200° C. |
| Raman | — | — |
| MB (moisture balance) | — | 0.20% weight loss upon equilibration at 5% RH<br>3.25% weight gain from 5% RH to 95% RH<br>1.44% weight loss from 95% RH to 5% RH |
| Post MB XRPD | — | Crystalline form and Amorphous |
| Hot Stage | 20x objective, 10° C./min up to 59.0° C., then 3° C./min | 23.2° C.: exhibits birefringence and extinction; 64.9° C.: reduced sample mass; 68.9° C.: melt; 78.1° C.: end of melt |
| NMR | DMSO-d6 | Consistent with structure, residual EtOAc said water |

2.2 Crystallization using Diethyl Ether

Diethyl ether (40 mL) was added to (3Z,5S)-5-(hydroxymethyl)-1-[(2'-methyl-1,1'-biphenyl-4-yl)carbonyl]pyrrolidin-3-one O-methyloxime (4.0 g). The solid was dissolved by swirling and the clear solution was left to stand at 18-23° C., Spontaneous nucleation occurred after ca. 10-15 minutes and the crystallization vessel and contents were allowed to stand undisturbed for 20 hours at 18-23° C. The crystals were isolated by filtration and dried under nitrogen for 4 hours at 18-23° C. Yield 338 g (84%), white crystals. Chemical purity 99.43%.

The resulting solid was analyzed by XRPD and confirmed to be crystalline (3Z,5S)-5-(hydroxymethyl)-1-[(2'-methyl-1,1'-biphenyl-4-yl)carbonyl]pyrrolidin-3-one O-methyloxime, FIGS. 6 and 8 are the DSC and TGA curves, respectively, obtained from testing this sample. Characterization data is presented in Table 5.

TABLE 5

Characterization data of crystalline (3Z,5S)-5-(hydroxymethyl)-1-[(2'-methyl-1,1'-biphenyl-4-yl)carbonyl]pyrrolidin-3-one O-methyloxime from diethyl ether

| Analytical Technique | Experiment Description | Results |
|---|---|---|
| XRPD | — | Crystalline form |
| DSC | 10° C./min, | Endo 76° C., baseline shift 124° C., Exo 233° C. |
| TGA | 25 to 350° C. | 5.3% weight loss at 200° C. |
| TG-IR | 20° C./min up to 190° C. | Diethyl ether up to 190° C. |

2.3 Other Crystallization attempts using Diethyl Ether

Numerous attempts at preparing the crystalline compound using diethyl ether were performed, as set forth in Table 6.

TABLE 6

Crystalline preparation attempt from amorphous 3Z,5S)-5-(hydroxymethyl)-1-[(2'-methyl-1,1'-biphenyl-4-yl)carbonyl]pyrrolidin-3-one O-methyloxime using diethyl ether

| Sample Wt/Ether Volume | Conditions[a] | Habit/Description[b] | XRPD Result |
|---|---|---|---|
| 53 mg 0.200 mL | 1. either addition with brief sonication | 1. most solid dissolved, then precipitating: blades, rosette clusters (B/E), insufficient liquid for decantation | — |
| | 2. air-dried RT 1 day | 2. blades, rosette clusters, glass (B/E), singles, no change in crystallinity of blades | |
| | 3. vac 66 to 77° C. 1 hour | 3. liquid | |
| 240 mg 0.897 mL | 1. ether addition | 1. most solid dissolved, then solid precipitating | Crystalline form |
| | 2. RT 1 day (no stir) | 2. blades, rosette clusters (B/E), singles | |
| | 3. decanted liquid, transferred solid | 3. initially damp, then seemed dry | |
| | 4. air-dried RT 5 hours | 4. no visual change, even by microscopy | |
| | 5. vac RT 20 hours | 5. no visual change, even by microscopy, 189 mg | |
| | 6. 23 mg vac 45° C. 65 hours | 6. no visual change, even by microscopy | Crystalline form |
| | 7. isolated crystals in P-N oil | 7. blade pieces (B/E, singles) | — |
| 3.16 g 8.000 mL | 1. ether addition 6 mL | 1. solid dissolving, then precipitating; became immobile from clumping | Crystalline form |
| | 2. ether addition 2 mL | 2. no change | |
| | 3. brief spatula stir, brief vortex | 3. "homogeneous" opaque slurry, very mobile | |
| | 4. RT 1 day (no stir) | 4. blades, agglomerates (B/E) | |
| | 5. vac filtered, washing with ether | 5. seemed dry | |
| | 6. gently crushed, homogenized | 6. powder, easily generated, thin layer | |
| | 7. vac 45° C. 62 hours | 7. slight crust | |
| | 8. scrape from glass, crush, homogenize | 8. — | |
| | 9. vac 45° C. 71 hours to constant weight | 9. slight crust | |
| | 10. transferred | 10. powder, easily generated, white, no change by microscopy, 2.65 g | |

[a]RT = ambient temperature; vac = vacuum; P-N = Paratone-N (non-GMP). Reported times and temperatures are approximate; temperatures measured by NIST-traceable thermometer.
[b]B = birefringence; E = extinction; singles = sample contains crystal(s) which appeared suitable for submission for single crystal x-ray.

One such preparation involved adding 0.897 ml of diethyl ether to 240 mg of amorphous (3Z,5S)-5-(hydroxymethyl)-1-[(2'-methyl-1,1'-biphenyl-4-yl carbonyl]pyrrolidin-3-one O-methyloxime and the mixture was left at ambient temperature tor about 24 hours. The liquid was decanted and the solid transferred to a dry container to be air dried for 5 hours. The solid was then vacuum-dried for 20 hours at ambient temperature. The resulting solid was analyzed by XRPD and confirmed to be the crystalline compound. The XRPD pattern from this sample is shown in FIG. 1.

23 mg of the solid was then further vacuum-dried at 45° C. for an additional 65 hours. The resulting solid was analyzed by XRPD and confirmed to be the crystalline compound. Characterization data is presented in Table 7.

TABLE 7

Characterization data of crystalline (3Z,5S)-5-(hydroxymethyl)-1-[(2'-methyl-1,1'-biphenyl-4-yl)carbonyl]pyrrolidin-3-one O-methyloxime from diethyl ether

| Analysis | Details | Result[a] |
|---|---|---|
| XRPD | indexed | Crystalline form |
|  | — | Crystalline form |
| TGA | 10° C./min | 5.4 wt % loss 25 to 200° C. |
| $^1$H NMR | (CD$_2$)$_2$SO | consistent with structure: residual ether |

[a]Temperatures rounded to nearest whole degree.

TESTING

Solid Stress Experiments

Solid stress experiments were conducted on crystalline (3Z,5S)-5-(hydroxymethyl)-1-[(2'-methyl-1,1'-biphenyl-4-yl)carbonyl]pyrrolidin-3-one O-methyloxime and amorphous (3Z,5S)-5-(hydroxymethyl)-1-[(2'-methyl-1,1'-biphenyl-4-yl)carbonyl]pyrrolidin-3-one O-methyloxime and the results shown below in Tables 8 and 9. Confirmed by XRPD, the results showed that the crystal form remained unchanged after stressing the material at 75% RH for 3 days. Stressing at 97% RH for the same time caused the material to deliquesce. A sample was also pressed at 10,000 psi for 1 minute and XRPD showed that it remained in crystalline form. However, grinding by hand for one minute produced a mixture of the crystalline compound and the amorphous compound, as shown by XRPD.

TABLE 8

Solid stress studies on crystalline (3Z,5S)-5-(hydroxymethyl)-1-[(2'-methyl-1,1'-biphenyl-4-yl)carbonyl]pyrrolidin-3-one O-methyloxime

| Solvent used for crystallization | Conditions | Habit/Description | XRPD Result |
|---|---|---|---|
| Ethyl Acetate | 75% RH, 3 days | Chunks, areas of birefringence | Crystalline form |
| Ethyl Acetate | 97% RH, 3 days | Deliquesced | — |
| Diethyl Ether | 10,000 psi, 1 minute | White Solid | Crystalline form |
| Diethyl Ether | 1 minute grind | White Solid | Crystalline form and Amorphous |

TABLE 9

Solid stress studies of amorphous (3Z,5S)-5-(hydroxymethyl)-1-[(2'-methyl-1,1'-biphenyl-4-yl)carbonyl]pyrrolidin-3-one O-methyloxime

| Conditions | Habit/Description | XRPD Result |
|---|---|---|
| 97% RH, 3 days | Deliquesced | — |
| 75% RH | 2.5% weight gain after 1 day 3.7% weight gain after 5 days 6.6% weight gain after 12 days 2.9% weight gain after 20 days White jagged flakes, chunks, no birefringence | Amorphous |
| 40° C./75% RH, 1 day | Oil drops | — |
| 40° C., 10 days | Rounded chunks | Amorphous |
| 70° C., 6 days | Rounded chunks, clear oil drops | Amorphous |
| 70° C., 1 day | Oil puddle | — |
| Ether stress, solid in solvent at ambient, 3 days (slurry) | White chunks, bits | Amorphous |
| Solid wet with ethyl ether | Needles/clustered blades with extinguishmen after 25 minutes Chunks, few areas of birefringence after 1 day at ambient Chunks, few areas with extinguish after 5 days ambient | — |
| Milling with 25 µL water, ~10 minutes | Sticky gum-like solid | — |
| Milling with 10µL toluene, ~70 minutes | Stick gum like solid after 10 minutes, sticky film by 70 minutes | — |

Solution Stress Experiments

Solution stress experiments were also conducted and the results presented in Table 10.

TABLE 10

Crystallization Solution Stress Experiments

| Solvent | Step | Experimental Details | Habit/Description | XRPD File |
|---|---|---|---|---|
| DCM | 1 | Sonication in ambient bath, ~60 minutes | Clear solution | — |
|  | 2 | Sonication and cooling, ~10 minutes | Clear solution |  |
|  | 3 | Placed in freezer for 11 days | Clear solution |  |
| EtOAc | 1 | Sonication in ambient bath, ~60 minutes | Clear solution | Crystalline form |
|  | 2 | Sonication and cooling, ~10 minutes | Clear solution |  |

TABLE 10-continued

Crystallization Solution Stress Experiments

| Solvent | Step | Experimental Details | Habit/Description | XRPD File |
|---|---|---|---|---|
| | 3 | Placed in freezer for 4 days, solvent then decanted | Grouped rounded blades, extinguish, soft and sticky | |
| | 4 | Hexane wash, dry under $N_2$ ~30 minutes | Chunks with extinguish | |
| 6:1 EtOAc:Water | 1 | Sonication in ambient bath, ~60 minutes | Milky white solution | |
| | 2 | Placed in freezer | chunks, few needles with extinguish | |
| Diethyl ether | 1 | Placed in freezer for 5 days | White solid, clustered needles with birefringence | Crystalline form |
| | 2 | Solvent decanted, left at ambient 1 day | Chunks, few needles w/extinguish | |
| | 3 | Solid slurried in ether 2 days | Small birefringent needles | |
| | 4 | Dry under $N_2$, 4 days | Small birefringent needles | |
| 1:4 Ether/Water | 1 | Left at ambient 1 day | Hazy solution, filtered, tacky film | — |
| 1,4-Dioxane | 1 | Sonication in ambient bath, ~60 minutes | Clear solution | — |
| | 2 | Sonication and cooling, ~10 minutes | Clear solution | |
| | 3 | Left at ambient | Clear solution | |
| IPA | 1 | Sonication in ambient bath, ~60 minutes | Clear solution | — |
| | 2 | Sonication and cooling, ~10 minutes | Clear solution | |
| | 3 | Placed in freezer for 11 days | Clear solution | |
| 1:2 IPA/Water | 1 | Left stirring at ambient overnight | Foggy with yellow liquid at base | — |
| | 2 | Yellow liquid decanted, water added to foggy solution, stirred | Suspension | |
| MEK | 1 | Sonication in ambient bath, ~60 minutes | Clear solution | — |
| | 2 | Sonication and cooling, ~10 minutes | Clear solution | |
| | 3 | Placed in freezer for 11 days | Clear solution | |
| 1:1 MeOH/Water | 1 | Left at ambient overnight | Clear solution w/yellow liquid at base | — |
| | 2 | Yellow liquid decanted, water added to precipitate solids in clear solution, stirred | Two layer system, both suspensions | |

Sonication of an example in ethyl acetate resulted in material which appeared as grouped blades by optical microscopy. After washing with hexanes and drying under nitrogen, the material appeared as irregular chunks, The sample was analyzed by XRPD and found to be crystalline (3Z,5S)-5-(hydroxymethyl)-1-[(2'-methyl-1,1'-biphenyl-4-yl)carbonyl]pyrrolidin-3-one O-methyloxime. In another example using diethyl ether, the mixture was frozen before mixing and drying under nitrogen to produce the crystalline form.

All other slurries did not produce any solid material.

Comparative Stability Study

Slurries of crystalline (3Z,5S)-5-(hydroxymethyl)-1-[(2'-methyl-1,1'-biphenyl-4-yl)carbonyl]pyrrolidin-3-one O-methyloxime and amorphous (3Z,5S)-5-(hydroxymethyl)-1-[(2'-methyl-1,1'-biphenyl-4-yl)carbonyl]pyrrolidin-3-one O-methyloxime were prepared by weighing directly into vials 100 mg of crystalline or amorphous material, About 3 mL of pH 7 phosphate buffer USP was added to each sample. Samples of each of the slurries were stirred in pH 7 phosphate buffer (USP) at 25° C. for 24 hours. At the end of 24 hours, the solvent was removed from the sample by pipetting out and solids allowed to air dry in the fumehood overnight. Solids were then submitted for XRPD analysis. Observations of the samples were made at various time intervals and are provided in Table 10. Both the samples first appeared as white powders. Pictures of the samples were taken at time points corresponding to 0.5 min, 15 min, 1 hour, 3 hours and 24 hours after adding the pH 7 phosphate buffer.

TABLE 10

Observation of Samples stirred to pH 7 phosphate trailer at 25° C.

| Time | Amorphous form (in pH 7 phosphate buffer) | Crystalline compound (in pH 7 phosphate buffer) |
|---|---|---|
| Before adding buffer | White power | White powder |
| T = 0 | White powder stuck at the bottom of the vial, difficult to disperse | White powder dispersed in buffer |
| T = 5 min | Thick white sticky mass | White powder dispersed in buffer |
| T = 15 min | Opaque sticky round lump | White powder dispersed in buffer |

TABLE 10-continued

Observation of Samples stirred to pH 7 phosphate trailer at 25° C.

| Time | Amorphous form (in pH 7 phosphate buffer) | Crystalline compound (in pH 7 phosphate buffer) |
|---|---|---|
| T = 1 hour | Opaque sticky round lump | White solid round lump, slightly sticky when stirred with a spatula and some dispersed solids |
| T = 3 hours | Opaque sticky material | White sticky material |
| T = 24 hours | Opaque sticky material | White sticky material |

Figure 4:
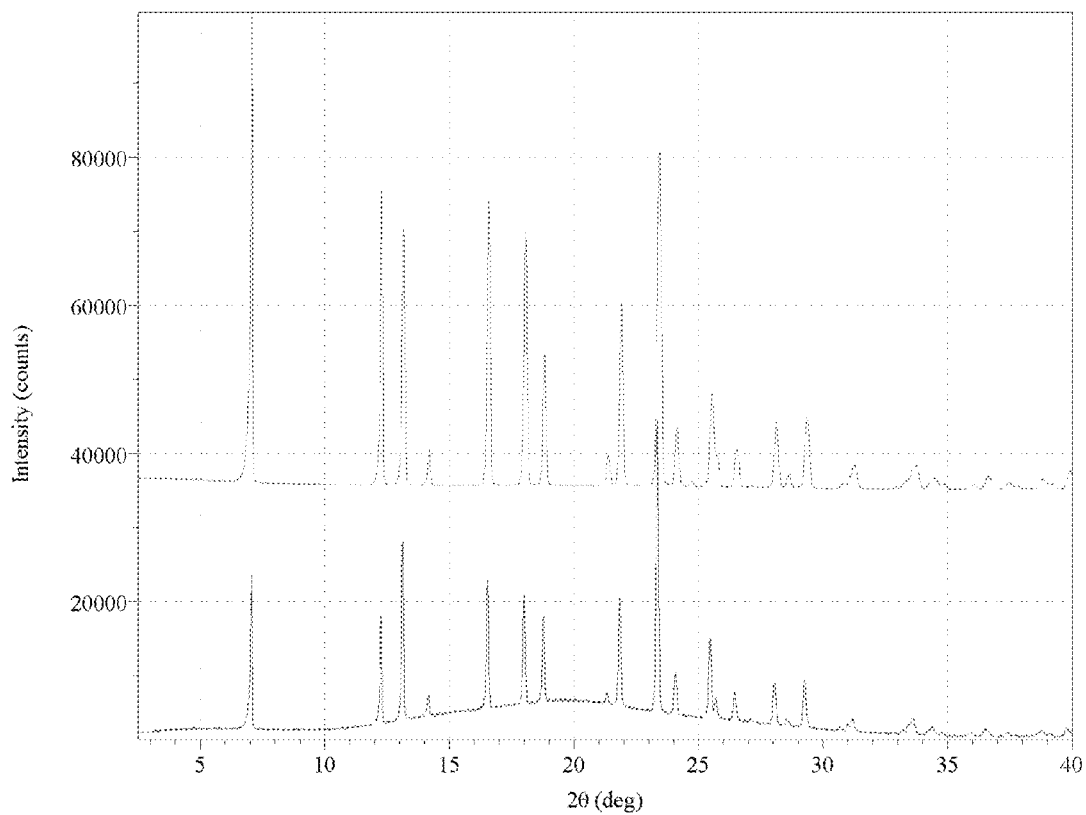
FIG. 4 shows XRPD pattern for crystalline (3Z,5S)-5-(hydroxymethyl)-1-[(2'-methyl-1,1'-biphenyl-4-yl)carbonyl]pyrrolidin-3-one O-methyloxime after synthesis compared to XRPD pattern for crystalline (3Z,5S)-5-(hydroxymethyl)-1-[(2'-methyl-1,1-biphenyl-4-yl)carbonyl] pyrrolidin-3-one O-methyloxime after stirring in pH 7 phosphate buffer for 24 hours.
Figure 5:
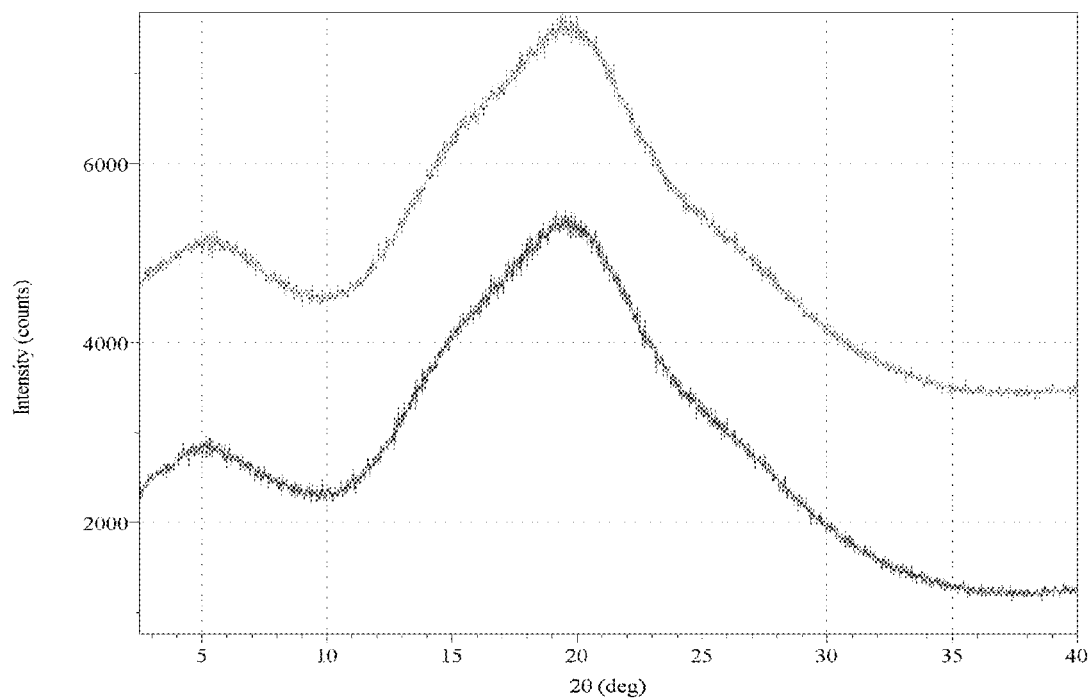
FIG. 5 shows XRPD pattern for amorphous (3Z,5S)-5-(hydroxymethyl)-1-[(2'-methyl-1,1-biphenyl-4-yl)carbonyl] pyrrolidin-3-one O-methyloxime after synthesis compared to XRPD pattern for amorphous (3Z,5S)-5-(hydroxymethyl)-1-[(2'-methyl-1,1-biphenyl-4-yl)carbonyl]pyrrolidin-3-one O-methyloxime after stirring in pH 7 phosphate buffer for 24 hours.

Amorphous (3Z,5S)-5-(hydroxymethyl)-1-[(2-methyl-1,1'-biphenyl-4-yl)carbonyl]pyrrolidin-3-one O-methyloxime converted to opaque sticky material after about 15 minutes. After about one hour, the slurry of crystalline (3Z,5S)-5-(hydroxymethyl)-1-[(2'-methyl-1,1-biphenyl-4-yl)carbonyl]pyrrolidin-3-one O-methyloxime showed formation of a white sticky material. Analysis of the XPRD pattern shows presence of amorphous phase after stirring amorphous (3Z,5S)-5-(hydroxymethyl)-1-[(2-methyl-1,1'-biphenyl-4-yl)carbonyl]pyrrolidin-3-one O-methyloxime for 24 hours. For a comparison. FIG. 5 shows the XRPD pattern for the amorphous form after synthesis and the XPRD pattern for amorphous form after stirring in pH 7 buffer for 24 hours. FIG. 4 shows the XRPD pattern for the crystalline compound after synthesis and the XPRD pattern for crystalline compound after stirring in pH 7 buffer for 24 hours, XPRD pattern of solids obtained on stirring crystalline (3Z,5S)-5-(hydroxymethyl)-1-[(2'-methyl-1,1'-biphenyl-4-yl)carbonyl]pyrrolidin-3-one O-methyloxime in the butter shows peaks consistent with those seen in the powder pattern of crystalline (3Z,5S)-5-(hydroxymethyl)-1-[(2'-methyl-1,1'-biphenyl-4-yl)carbonyl]pyrrolidin-3-one O-methyloxime (FIG. 4). Slight peak shift is seen at higher 2θ angles when comparing the XRPD patterns of the before and after samples of crystalline (3Z,5S)-5-(hydroxymethyl)-1-[(2'-methyl-1,1'-biphenyl-4-yl)carbonyl]pyrrolidin-3-one O-methyloxime. Some diffused scatter is also seen in the powder pattern of the solids obtained from the slurry of crystalline (3Z,5S)-5-(hydroxymethyl)-1-[(2'-methyl-1,1'-biphenyl-4-yl)carbonyl]pyrrolidin-3-one O-methyloxime.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. Crystalline (3Z,5S)-5-(hydroxymethyl)-1-[(2'-methyl-1,1'-biphenyl-4-yl)carbonyl]pyrrolidin-3-one O-methyloxime, wherein said crystalline compound is characterized by an X-ray powder diffraction (XRPD) pattern substantially as illustrated in FIG. 1.

2. Crystalline (3Z,5S)-5-(hydroxymethyl)-1-[(2'-methyl-1,1'-biphenyl-4-yl)carbonyl]pyrrolidin-3-one O-methyloxime, wherein said crystalline compound exhibits characteristic peaks at diffraction angle 2-theta degrees appearing at least at about 23.34, about 13.13, and about 7.05, as measured by XRPD.

3. Crystalline (3Z,5S)-5-(hydroxymethyl)-1-[(2'-methyl-1,1'-biphenyl-4-yl)carbonyl]pyrrolidin-3-one O-methyloxime, wherein said crystalline compound is characterized by a differential scanning calorimetry curve substantially as illustrated in FIG. 6 or FIG. 7.

4. Crystalline (3Z,5S)-5-(hydroxymethyl)-1-[(2'-methyl-1,1'-biphenyl-4-yl)carbonyl]pyrrolidin-3-one O-methyloxime, wherein said crystalline compound is characterized by a thermo-gravimetric analysis curve substantially as illustrated in FIG. 8 or FIG. 9.

5. A pharmaceutical composition comprising the crystalline compound of claim 2 and a pharmaceutically acceptable excipient.

* * * * *

UNITED STATES PATENT AND TRADEMARK OFFICE
CERTIFICATE OF CORRECTION

PATENT NO. : 9,718,772 B2
APPLICATION NO. : 14/735215
DATED : August 1, 2017
INVENTOR(S) : Andre Chollet It is certified that error appears in the above-identified patent and that said Letters Patent is hereby corrected as shown below:

On the Title Page

In ABSTRACT, replace "preterm labor, and tor" with --preterm labor, and for--.

Page 2, in M. Caira, replace "Polymophism" with --Polymorphism--.

In the Specification

Column 1, Lines 23-24, replace "(3Z,5S)-5-(hydroxymethyl)-1- [(2'-methyl-1,1-biphenyl-4-yl)carbonyl]pyrrolidin-3-one O-methyloxime" with
--(3Z,5S)-5-(hydroxymethyl)-1- [(2'-methyl-1,1'-biphenyl-4-yl)carbonyl]pyrrolidin-3-one O-methyloxime--.

Column 2, Line 17, replace "(ART), Although" with --(ART). Although--;
Lines 39-40, replace "sufficient benefit" with --sufficient benefit.--;
Line 52, replace "might represents an" with --might represent an--;
Line 57, replace "are used oil-label." with --are used off-label.--.

Column 3, Line 35, replace "Specifically. Non-peptide" with --Specifically, non-peptide--;
Line 37, replace "WO 2002/07474" with --WO 2002/074741--;
Line 39, replace "as mixtures of isomers, arc" with --as mixtures of isomers, are--;
Line 42, replace "(3Z,5S)-5-(hydroxymethyl)-1- [(2'-methyl-1,1-biphenyl-4-yl)carbonyl]pyrrolidin-3-one O-methyloxime" with
--(3Z,5S)-5-(hydroxymethyl)-1- [(2'-methyl-1,1'-biphenyl-4-yl)carbonyl]pyrrolidin-3-one O-methyloxime--;
Line 48, replace "labor, in particular" with --labor. In particular--;
Line 58, replace "(3Z,5S)-5-(hydroxymethyl)-1- [(2'-methyl-1,1-biphenyl-4-yl)carbonyl]pyrrolidin-3-one O-methyloxime" with
--(3Z,5S)-5-(hydroxymethyl)-1- [(2'-methyl-1,1'-biphenyl-4-yl)carbonyl]pyrrolidin-3-one O-methyloxime--.

Signed and Sealed this
Second Day of January, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,718,772 B2

Column 4, Line 45, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 49, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl)pyrrolidin-3-one O-methyloxime--;

Line 52, replace "(3Z,5S)-5-(hydroxymethyl)-1 [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl)pyrrolidin-3-one O-methyloxime--;

Lines 56-57, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 60, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--.

Column 5, Line 2, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Lines 9-10, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 66, replace "about 40x" with --about 40°C--;
Line 67, replace "about 40*C" with --about 40°C--.

Column 6, Line 14, replace "activity Include preterm" with --activity include preterm--;
Line 58, replace "development, Basic" with --development. Basic--.

Column 7, Line 6, replace "fuel" with --Inel--;
Line 11, replace "a approximately" with --at approximately--;
Line 36, replace "generated by air, Sofler slits" with --generated by air. Soller slits--.

Column 9, Line 46, replace "analysts" with --analysis--;
Line 47, replace "2920, The" with --2920. The--;
Line 48, replace "for energy And temperature" with --for energy and temperature--;
Line 51, replace "accurately Recorded" with --accurately recorded--;
Line 52, replace "nitrogen Purge at a rate" with --nitrogen purge at a rate--;
Line 55, replace "cycling Experiment" with --cycling experiment--;
Line 58, replace "temperature again, Cooling it" with --temperature again, cooling it--;

CERTIFICATE OF CORRECTION (continued)

U.S. Pat. No. 9,718,772 B2

Line 61, replace "change in Temperature" with --change in temperature--;
    Line 62, replace "presence of Solvates" with --presence of solvates--;
    Line 65, replace "calibrated Using" with --calibrated using--;
    Line 66, replace "pan and Inserted into" with --pan and inserted into--.

Column 10, Line 2, replace "The Sample having" with --The sample having--;
    Line 3, replace "ambient Temperature to" with --ambient temperature to--;
    Line 46, replace "certain embodiment, alter" with --certain embodiment, after--;
    Line 55, replace "1%. including" with --1%, including--.

Column 11, Line 3, replace "storage period," with --storage period.--;
    Line 23, replace "embodiments, if may also" with --embodiments, it may also--;
    Line 37, replace "as a gel an ointment" with --as a gel, an ointment--;
    Line 39, replace "glycerol alcohol" with --glycerol, alcohol--;
    Line 43, replace "raonolauriate" with --monolaurate--;
    Line 60, replace "also Include lactose" with --also include lactose--;
    Line 67, replace "combinations thereof The" with --combinations thereof. The--.

Column 12, Line 46, replace "pharamaceutical-grade" with --pharmaceutical-grade--;
    Line 63, replace "chlorbutanol" with --chlorobutanol--.

Column 13, Line 2, replace "tiethyl curate" with --triethyl citrate--;
    Line 9, replace "Eudragst®" with --Eudragit®--;
    Line 10, replace "Sureterie® (Coloreon" with --Sureteric® (Colorcon--;
    Line 32, replace "submiae, rofecoxib, celceoxib" with --sulindac, rofecoxib, celecoxib--;
    Lines 48-49, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;
    Line 51, replace "preterm labor," with --preterm labor.--;
    Lines 56-57, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--.

Column 14, Line 31, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;
    Line 33, replace "parenterals" with --parenterally--;
    Line 40, replace "20minutes" with --20 minutes--;
    Lines 45-46, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

CERTIFICATE OF CORRECTION (continued)
U.S. Pat. No. 9,718,772 B2

Line 65, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--.

Column 15, Line 2, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 9, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 20, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 22, replace "solid y then dissolved" with --solid is then dissolved--;

Line 40, replace "(3Z,5S)-5-(hydroxymethyl)-1-[(2'-methyl-1,1-biphenyl-4-yl)carbonyl]pyrrolidin-3-one O-methyloxime" with --(3Z,5S)-5-(hydroxymethyl)-1-[(2'-methyl-1,1'-biphenyl-4-yl)carbonyl]pyrrolidin-3-one O-methyloxime--;

Line 64, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--.

Column 16, Line 2, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Lines 5-6, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 8, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 10, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 12, replace "are tor example" with --are for example--;

Lines 14-15, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Lines 16-17, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 20, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 61, replace "o-tolyboronic" with --o-tolylboronic--;

Line 66, replace "completion (The reaction" with --completion (the reaction--.

Column 17, Line 6, replace "vigorously tor 30" with --vigorously for 30--;

Line 15, replace "by 'H NMR" with --by $^1$H NMR--;

Line 19, replace "val)." with --vol).--.

Column 18, Line 45, replace "rinse of wafer" with --rinse of water--;

Line 58, replace "0to 5°C" with --0 to 5°C--.

Column 19, Lines 1-2, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 43, replace "1 to 3 hours). 7" with --1 to 3 hours).--;

Line 48, replace "(2×300 L" with --(2×3.00 L--;

Line 50, replace "(2×1 20 L" with --(2×1.20 L--;

Line 67, replace "paper, The filter-cake" with --paper. The filter-cake--.

Column 20, Line 9, replace "1 to 2hours" with --1 to 2 hours--.

Column 21, Line 4, replace "sat, aq," with --sat.aq.--;

Lines 53-54, replace "(3Z,5S)-5-(hydroxymethyl)-1- [(2'-methyl-1,1-biphenyl-4-yl)carbonyl]pyrrolidin-3-one O-methyloxime" with --(3Z,5S)-5-(hydroxymethyl)-1- [(2'-methyl-1,1'-biphenyl-4-yl)carbonyl]pyrrolidin-3-one O-methyloxime--;

Line 67, replace "axeotropic" with --azeotropic--.

Column 22, Line 54, replace "0.8 val)" with --0.8 vol)--.

Column 23, Line 14, replace "pure form (3Z,5S)-5-(hydroxymethyl)-1- [(2'-methyl-1,1-biphenyl-4-yl)carbonyl]pyrrolidin-3-one O-methyloxime" with --pure form of (3Z,5S)-5-(hydroxymethyl)-1- [(2'-methyl-1,1'-biphenyl-4-yl)carbonyl]pyrrolidin-3-one O-methyloxime--;

CERTIFICATE OF CORRECTION (continued)
U.S. Pat. No. 9,718,772 B2

Line 19, replace "oximc" with --oxime--;
      Line 26, replace "(No. 068). and" with --(No. 068), and--;
      Line 44, replace "oximc" with --oxime--;
      Line 45, replace "ovime ester" with --oxime ester--.

Column 24, Line 35, replace "The fractious" with --The fractions--.

Column 25, Line 52, replace "24 hours, The oven" with --24 hours. The oven--.

Column 29, in Table 7, replace "$(CD_2)_2SO$" with --$(CD_3)_2SO$--.

Column 30, Line 41, replace "extinguishmen" with --extinguishment--;
      Line 48, replace "Stick gum" with --Sticky, gum--.